US012654025B2

(12) United States Patent
Holzer et al.

(10) Patent No.: US 12,654,025 B2
(45) Date of Patent: Jun. 16, 2026

(54) DEVICES AND METHOD FOR PREVENTION AND TREATMENT OF FUNGAL AND BACTERIAL MICROORGANISMS

(71) Applicant: ZERO CANDIDA LTD., Dalton (IL)

(72) Inventors: Asher Holzer, Dalton (IL); Eli Ben Haroosh, Dalton (IL)

(73) Assignee: ZERO CANDIDA LTD., Dalton (IL)

( * ) Notice: Subject to any disclaimer, the term of this patent is extended or adjusted under 35 U.S.C. 154(b) by 0 days.

(21) Appl. No.: 18/707,595

(22) PCT Filed: Mar. 9, 2023

(86) PCT No.: PCT/IL2023/050243
§ 371 (c)(1),
(2) Date: May 5, 2024

(87) PCT Pub. No.: WO2023/170689
PCT Pub. Date: Sep. 14, 2023

(65) Prior Publication Data
US 2025/0001195 A1      Jan. 2, 2025

Related U.S. Application Data

(60) Provisional application No. 63/318,332, filed on Mar. 9, 2022.

(51) Int. Cl.
*A61N 5/06*      (2006.01)
*A61K 31/10*      (2006.01)
*A61K 41/00*      (2020.01)
*A61P 31/10*      (2006.01)
(52) U.S. Cl.
CPC ............ *A61N 5/0603* (2013.01); *A61K 31/10* (2013.01); *A61K 41/0057* (2013.01);
(Continued)

(58) Field of Classification Search
CPC .... A61N 5/0603; A61N 5/062; A61N 5/0624; A61N 2005/0611; A61N 2005/0626; A61N 2005/0663; A61N 5/0622; A61P 31/10; A61K 31/10; A61K 41/0057; A61H 19/44; A61H 19/34; A61H 19/40; A61H 23/00; A61H 23/0263; A61H 7/003;
(Continued)

(56) References Cited

U.S. PATENT DOCUMENTS

| | | | | | |
|---|---|---|---|---|---|
| 3,404,682 A | * | 10/1968 | Waldron | ................. | A61F 13/26 |
| | | | | | 128/838 |
| 2006/0105963 A1 | * | 5/2006 | Yang | ....................... | A61P 15/02 |
| | | | | | 514/23 |
| 2006/0167531 A1 | * | 7/2006 | Gertner | ................ | A61N 5/0603 |
| | | | | | 607/86 |
| 2006/0195165 A1 | | 8/2006 | Gertner et al. | | |

(Continued)

OTHER PUBLICATIONS

International Search Report for PCT/IL2023/050243 Completed May 28, 2023; mailed Jul. 20, 2023 4 pages.
Written Opinion for PCT/IL2023/050243 Completed May 28, 2023; mailed Jul. 20, 2023 9 pages.

*Primary Examiner* — Adam Z Minchella
(74) *Attorney, Agent, or Firm* — The Law Office of Joseph L. Felber

(57) ABSTRACT

The invention features methods of inhibiting the growth of, or killing, fungal-, bacterial-, and viral-infections by exposure to light, optionally together with one or more active substances such as therapeutics, hormones, and buffer-compounds.

23 Claims, 14 Drawing Sheets

100

106

(52) U.S. Cl.
CPC ........... *A61N 5/062* (2013.01); *A61N 5/0624* (2013.01); *A61P 31/10* (2018.01); *A61N 2005/0611* (2013.01); *A61N 2005/0626* (2013.01); *A61N 2005/0663* (2013.01)

(58) Field of Classification Search
CPC .......... A61H 23/006; A61H 2201/0153; A61H 2201/10; A61H 2201/5005; A61H 2201/501; A61H 2201/5015; A61H 2201/5038; A61H 2201/5061; A61H 2201/5097; A61H 2230/045; A61H 2230/085; A61H 2230/208

See application file for complete search history.

(56) References Cited

U.S. PATENT DOCUMENTS

| | | | |
|---|---|---|---|
| 2011/0190689 A1* | 8/2011 | Bennett ............... | A61B 5/6846 |
| | | | 604/21 |
| 2016/0008624 A1 | 1/2016 | Grossman | |
| 2016/0129278 A1* | 5/2016 | Mayer .................. | A61N 5/0624 |
| | | | 607/92 |
| 2016/0151639 A1* | 6/2016 | Scharf .................. | A61N 5/0624 |
| | | | 607/92 |
| 2017/0071715 A1* | 3/2017 | Henriksson ............ | A61H 21/00 |
| 2017/0333728 A1 | 11/2017 | Sentis et al. | |
| 2018/0361170 A1* | 12/2018 | Klang .................. | A61N 5/0603 |
| 2025/0205510 A1* | 6/2025 | Harris .................. | A61N 5/0624 |

* cited by examiner

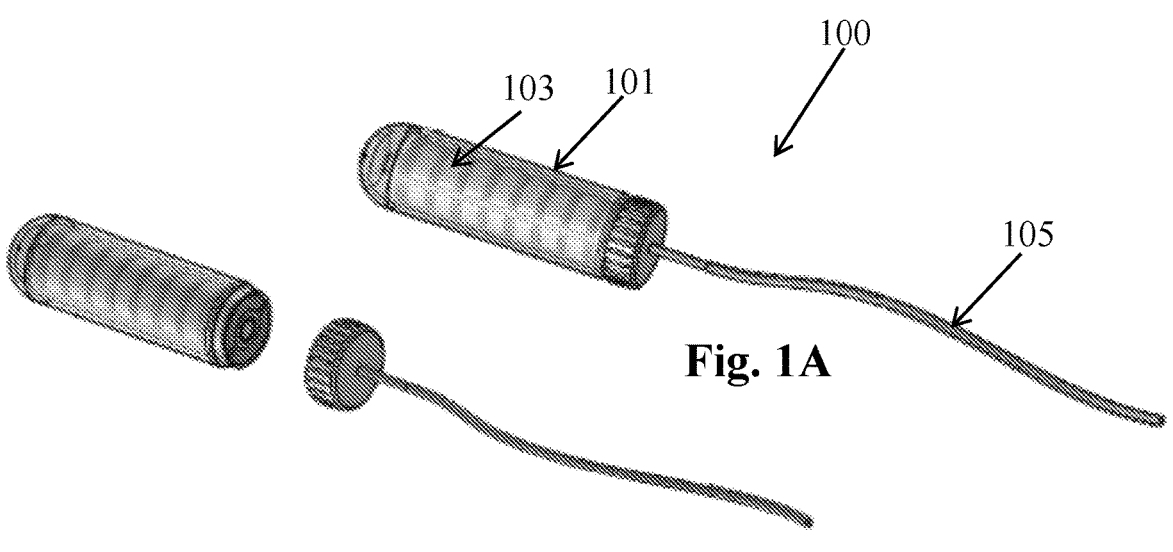
Fig. 1A
Fig. 1B
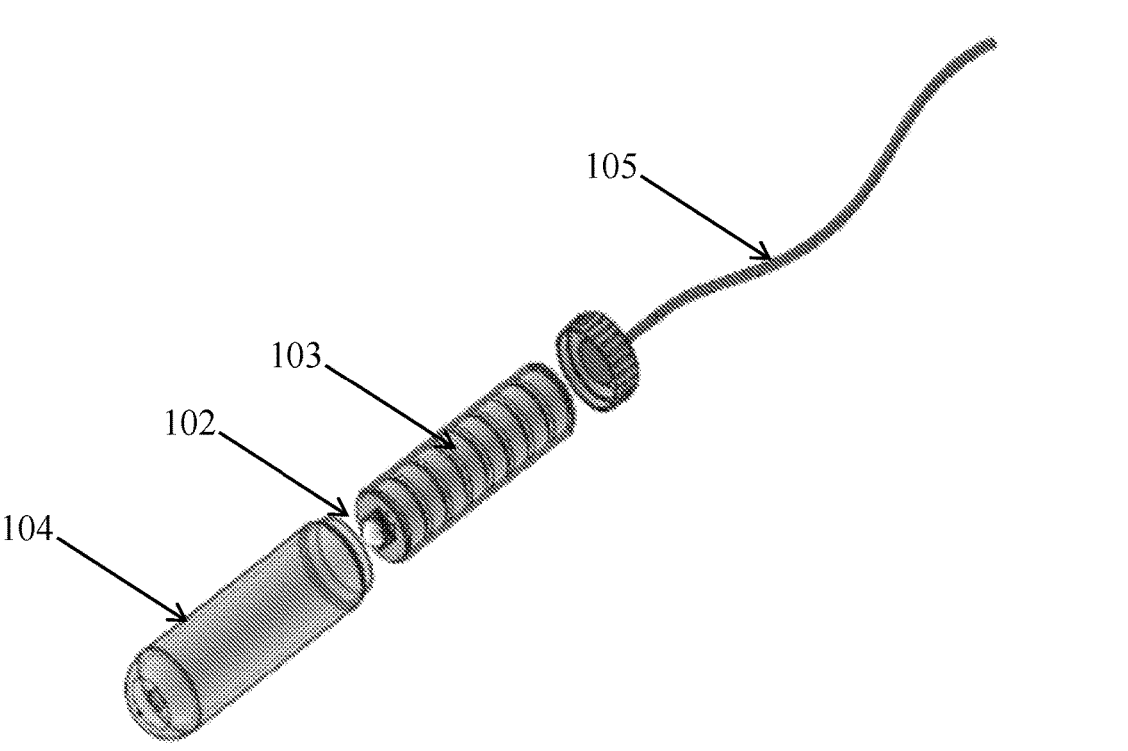
Fig. 1C

100

106 protrusions 116 camera

100

ILTD activation &
insertion into a cavity

optionally, measuring various parameters
(pH, temp., taking images, etc.)

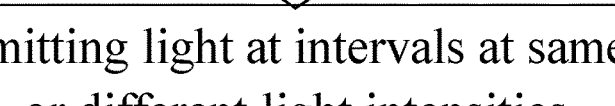

emitting light at intervals at same
or different light intensities optionally, emitting the light at
specific directions

Fig. 10A

ILTD activation &
insertion into a cavity optionally, measuring various parameters
(pH, temp., taking images, etc.)

emitting constant light or at intervals at same or
different light intensities (optionally at specific
directions), while releasing one or more active agents,
either constantly or periodically according to need

Fig. 10B

| PD | Pulse power |
|----|-------------|
| W | Pulse width |
| DD | Duty cycle |
| INT | *Train interval* |
| TD | *Train Duration* |
| P | Pulse frequency |

DEVICES AND METHOD FOR PREVENTION AND TREATMENT OF FUNGAL AND BACTERIAL MICROORGANISMS

CROSS REFERENCE TO RELATED APPLICATIONS

This application is a National Phase of PCT Patent Application No. PCT/IL2023/050243 having International filing date of Mar. 9, 2023, which claims the benefit of priority of U.S. Provisional Patent Application No. 63/318, 332, filed Mar. 9, 20222, the contents of which are all incorporated herein by reference in their entirety.

TECHNICAL FIELD

The invention relates to devices and methods for controlling infections, particularly to fungal-, such as yeast, and bacterial-infections. Specifically, the present invention relates to the treatment and prevention of vaginal infections.

BACKGROUND

Vaginitis is characterized by the inflammation of the vagina that results in discharge, itching and pain. The cause is usually a change in the normal balance of vaginal bacteria or an infection. Infection symptoms range from mucus like discharge, itching, aching, pain during intercourse to odor. The vaginal infections often have multiple causes that present challenging cases for treatment. When the balance between naturally occurring yeast and bacteria is distorted or when other types of bacteria are present in the vagina, vaginitis happens. However, when one cause is treated another problem might arise: e.g., pathogens resistance or mutations due to antibiotic treatment, reduction in good bacteria that allows yeast propagation and infection (typically *Candida albicans*). Further, a change in pH balance or introduction of foreign bacteria in the vagina may also lead to infectious vaginitis.

Bacterial vaginosis, a.k.a. vaginal bacteriosis or *Gardnerella* Vaginitis, is a disease of the vagina caused by excessive bacteria growth. Bacterial vaginosis increases the risk of, e.g.: (i) infection by other sexually transmitted infections, such as HIV/AIDS; and (ii) early delivery among pregnant women. Usually, treatment is with antibiotics administered either orally or vaginally. However, over 10% of the cases are irresponsive to antibiotics, and recurrence rates of up to 80% have been documented.

Candidiasis, more commonly referred to as a Yeast Infection, is commonly caused by an overgrowth of a fungus called *Candida albicans* in the vagina. *Candida* is yeast, a type of fungus. Yeast is always present in the vagina in small numbers, however symptoms appear with overgrowth, due to various reasons, such as when normal acidity of the vagina changes or when hormonal balance changes. Frequently occurring yeast infections may be a sign of more serious overarching health problem such as diabetes or a compromised immune system. Recurrent infections may also be due to use of antibiotic medications.

Contrary to antibacterial therapy, antifungal treatment is limited to a very small number of drug substances, which can also be topical or systemic. Topical antifungals are generally considered as first-line therapy for uncomplicated, superficial, relatively localized fungal infections due to their high efficacy and low potential for systemic adverse effects. Systemic antifungal agents are absorbed and delivered to the body through the blood stream. The oral route is usually the safest, the most economical, and the easiest route for systemic antifungal drugs. However, antifungal pills affect the entire body, and may cause side effects such as nausea, headaches, and abdominal pain. Topical antifungal creams and suppositories have fewer side effects than oral antifungal medications since they only exert a localized effect on the genital region. However, topical medications can be messy and uncomfortable.

Antifungal therapy has been shown to be ineffective in up to 20% of cases. Treatment is considered to have failed if the symptoms do not clear within 7-14 days. In addition, resistance to antifungal agents increases over time, with drug-resistant fungal strains becoming increasingly common causes of infection in high-risk patient groups such as HIV/AIDS patients. Accordingly, alternative antifungal strategies are being actively sought.

Severe forms of infection are hard to treat, and frequently require more aggressive and long-term therapy, as is the case with chronic, recurrent cases. Additionally, incomplete treatments often result in drug resistant infections therefore full course of therapy should be adhered to.

Accordingly, it is important to provide effective therapeutic and/or prophylactic anti-microbial and anti-fungal treatments, which are both inexpensive and logistically simple to deliver to the patients. Also, it is important to avoid the known phenomenon of vicious cycle of bacterial infection-*candida* infection.

Various alternative treatments were developed, which are based on illumination to treat various infections, such as devices with a photo-sensitizing agent for treating yeast infection. In photodynamic antimicrobial chemotherapy (PACT), a combination of a sensitizing drug and visible light causes selective destruction of microbial cells. The ability of a light-drug combination to kill microorganisms is well known, and various studies have shown PACT to be highly effective in in-vitro destruction of viruses, protozoa, gram-positive and gram-negative bacteria and fungi. Light radiation at certain wavelengths causes the death or retarded growth of fungal pathogens residing in human tissue. Reactive oxygen species (ROS) can be generated under light-tissue/fungi interaction. Light at certain wavelengths has high efficiency in stimulating generation of ROS in fungal infected areas. Higher power (as compared to traditional low light therapy) of light radiation and prolonged exposure time on tissue creates a fatal concentration of ROS, which is toxic to the pathogen, resulting the retardation or death of the fungi. Under the same circumstances of radiation, the light does not significantly affect healthy human tissue around the infected area. Light radiation only affects local tissue within the radiation zone and has no systemic toxicity.

Some solutions were developed to introduce light intra-vaginally, namely intravaginal treatment devices (ITD) that provides therapeutic light and optionally fluid treatments. Some ITDs can use illumination to gather image data used to identify the vagina's condition, monitor the treatment process, and evaluate treatment efficacy. Specific frequency light emissions and associated fluids are used to reduce overabundant flora, at least assist in elimination of fungi, viruses and bacteria, and improves detection. Some ITDs also have a built-in optics assembly (camera, light sources, etc.) for capturing intravaginal still images and video of vaginal channels, cervix, cervical channels, uterus, and fallopian tubes. Therapy procedures using such ITDs may be preset or programmed to deliver continuous, periodic and scheduled performance with various underlying parameters defined in the preset or programming processes.

Other solutions use laser-emitting device for directing a laser beam towards the vagina wall for treating the mucosa of the vaginal canal. This enables to prevent and treat atrophic vaginitis, which is a pathological condition characterized by an inflammation of the vaginal mucosa with progressive decrease of the mucosa thickness due to the loss of collagen structure.

Although light therapy treatment of various bacterial, fungal and viral infections intravaginally is known, such treatment is usually achieved through chemical or drug therapies, which affect internal functioning of the vagina and uterus since the chemicals being used are in the form of paste, gel or liquid that lead to unwanted harsh chemical reactions or various complications. In addition, all proposed known light therapies require the use of sophisticated and miniature devices that the prior art references fail to disclose or implement.

Since oral antifungal medications carry the risk of significant side effects, and since topical solutions are messy, inconvenient and have limited effectivity, there is a need for a product that allows for the treatment of vaginal infections (yeast, viral and bacterial) quickly and simply without systemic effects. Accordingly, the present invention provides intravaginal light-based treatment devices (ILTDs) that are simple to use, highly effective in treating various vaginal infections, has little to none side-effects, and are cost effective.

The above mentioned shortcomings, disadvantages and problems are addressed herein, as detailed below.

SUMMARY

In a first aspect, the present invention provides an intravaginal light-based treatment device (ILTD) (100) for treating patient's vaginal disorders, the device comprises: (a) a main body (101); (b) a light source (102); (c) a power source (103); (d) optionally, a coating (104) over said main body (101); and (e) a tether (105), wherein said light source is designed to emit pulsed light having at least one predefined wavelength suitable for treating said vaginal disorders, and said main body (101) and coating (104) are designed to allow said light to pass through and reach vaginal tissue; said light source is designed to emit said light at predefined intervals and intensities suitable for treating said vaginal disorders; and said tether (105) is connected to said main body (101) and is designed to be used for retracting the ILTD outside from the patient's vagina.

In a second aspect, the present invention provides an intravaginal light-based treatment device (ILTD) (100) for treating patient's vaginal disorders, the device comprises: (a) a main body (101); (b) a light source (102); (c) a power source (103); (d) optionally, a coating (104) over said main body (101); (e) a tether (105); and (f) one or more active agents selected from: therapeutic agents, drugs, antipetry drugs, antibiotics, moisture materials, hormones, photosensitizers, therapeutics, buffer material, and/or biome, or any combination thereof, wherein said light source is designed to emit either a continuous/constant light or a pulsed light at predefined intervals and intensities suitable for treating said vaginal disorders, having at least one predefined wavelength suitable for treating said vaginal disorders, and said main body (101) and coating (104) are designed to allow said light to pass through and reach vaginal tissue; said device or coating is designed to release said one or more active agents into the vagina; and said tether (105) is connected to said main body (101) and is designed to be used for retracting the ILTD outside from the patient's vagina.

In a third aspect, the present invention provides kits for treating patient's vaginal disorders, said kits comprising one or more ILTDs as defined above.

In a fourth aspect, the present invention provides kits for monitoring and diagnosing a patient's vaginal health condition, the kits comprising two or more ILTDs according to any of the embodiments above.

In a fifth aspect, the present invention provides a light-based method of treatment or prophylaxis of a vaginal disorder in a woman, the method comprising: (a) providing an intravaginal light-based treatment device (ILTD) of the invention; (b) inserting said ILTD into the vagina of the woman; and (c) activating the ILTD thereby illuminating the vagina interior, and releasing said one or more active agents when present in the ILTD.

In a sixth aspect, the present invention provides methods of diagnosing or monitoring of various conditions and disorders in a patient's vagina by inserting into the vagina the ILTD of the invention.

In a seventh aspect, the present invention provides methods to illuminate different parts of the vagina altering among various sites thus illuminating different areas for different period of times.

BRIEF DESCRIPTION OF THE DRAWINGS

For a better understanding of various embodiments of the invention and to show how the same may be carried into effect, reference will now be made, by way of example, to the accompanying drawings, in which:

FIGS. 1A-1D are schematic illustrations of an intravaginal light-based treatment device (ILTD) according to the invention: FIG. 1A is an assembled ILTD; FIG. 1B is the same ILTD with its rear cap opened; FIG. 1C is an exploded view of the ILTD; and FIG. 1D is an exploded view of a different ILTD equipped with a pH-sensor near its light source.

FIG. 2A shows the ILTD and a separated coating; and FIG. 2B is an exploded view of the ILTD.

FIG. 5A shows the assembled ILTD; and FIG. 5B is an illustration of the ILTD with its coating removed.

FIG. 6A shows the assembled ILTD; and FIG. 6B is an illustration of the ILTD's main body disassembled from the external unit.

FIG. 7A shows the assembled ILTD; FIG. 7B is an illustration of an exploded view of the ILTD's main body; and FIG. 7C is an enlargement of the camera section circled in FIG. 7B.

FIG. 8A shows the assembled ILTD; and FIG. 8B is an exploded view of the ILTD.

FIGS. 10A-10B are diagrams illustrating possible mode of activation of the ILTD according to some embodiments of the invention.

Figure 1D:
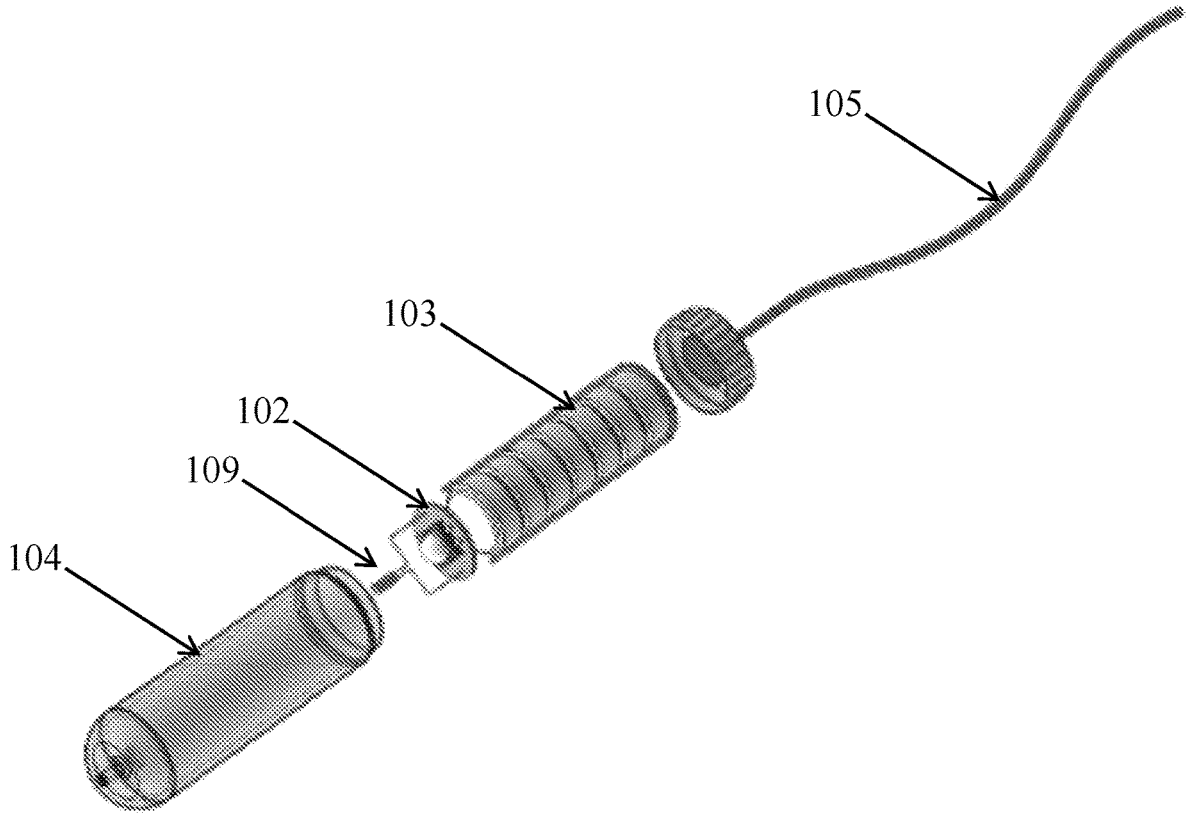

Structural details of the invention are shown to provide a fundamental understanding of the invention, the description, taken with the drawings, making apparent to those skilled in the art how the several forms of the invention may be embodied in practice.

DETAILED DESCRIPTION

*Candida albicans*, a dimorphic, imperfect yeast, is a significant human pathogen that can cause superficial or invasive diseases and is the most common cause of candidiasis. *C. albicans* is an opportunistic pathogen that primarily infects immunocompromised or immunosuppressed individuals.

Candidiasis and other yeast infections are usually treated with antifungal agents, such as nystatin, ciclopirox, and imidazole creams, which may be administered in the form of a topical cream, suspension or suppository. Other drugs, such as amphotericin B, may be administered orally, but are usually accompanied with unpleasant side effects and cannot be administered over an extended time period. However, relapse after successful treatment is common.

Other vaginal infections, such as viral (e.g., herpes) and bacterial (e.g., over growth of one of several bacteria naturally found in the vagina, such as when "good" lactobacilli outnumber "bad" anaerobes, or vise-versa), are also common, and treatment thereof involves similar treatment methodologies, i.e., topical- or oral-treatment, with similar disadvantages as noted above.

In addition, it is known that pH, temperature, and humidity influence various infections in terms of onset and development, and often such infections appear because of changes in pH, temperature, and humidity, e.g., due to a pH alteration in the vagina.

The above mentioned and other problems raise a need for a more effective treatment of vaginal disorders and infections, which ideally provides all the advantages of known therapies and overcomes known disadvantages thereof, while enabling reducing or elimination relapse of the treated condition or disorder.

The invention is based in part upon the discovery that exposing of yeasts, *candida*, bacteria and viruses of a variety of strains to light of certain wavelengths kills them, reduces their amount, reduces their ability to reproduce, and/or attenuates their growth and ability to cause harm. Such effects may be influenced by adjusting the pH to around 4 when treating fungi, and another pH level when treating bacteria, and may further be improved when combining it with the administration of specific therapeutics.

Accordingly, in a first aspect, the present invention provides an intravaginal light-based treatment device (ILTD) (100) for treating patient's vaginal disorders, the device comprises: (a) a main body (101); (b) a light source (102); (c) a power source (103); (d) a coating (104) over said main body (101); and (e) a tether (105), wherein said light source is designed to emit a light having at least one predefined wavelength suitable for treating said vaginal disorders, and said coating (104) is designed to allow said light to pass and reach vaginal tissue; and said tether (105) is connected to said main body (101) and is designed to be used for retracting the ILTD outside from the patient's vagina.

In certain embodiments, the present invention provides an intravaginal light-based treatment device (ILTD) (100) for treating patient's vaginal disorders, the device comprises: (a) a main body (101); (b) a light source (102); (c) a power source (103); (d) optionally, a coating (104) over said main body (101); and (e) a tether (105), wherein said light source is designed to emit pulsed light having at least one predefined wavelength suitable for treating said vaginal disorders, and said main body (101) and coating (104) are designed to allow said light to pass through and reach vaginal tissue; said light source is designed to emit said light at predefined intervals and intensities suitable for treating said vaginal disorders; and said tether (105) is connected to said main body (101) and is designed to be used for retracting the ILTD outside from the patient's vagina.

In certain embodiments, the present invention provides an intravaginal light-based treatment device (ILTD) (100) for treating patient's vaginal disorders, the device comprises: (a) a main body (101); (b) a light source (102); (c) a power source (103); (d) optionally, a coating (104) over said main body (101); and (e) a tether (105), wherein said light source is designed to emit continuous or pulsed light at different locations of the vagina, altering among them, wherein the altering between the different sites may be controlled by, e.g., identification of temperature at each site, moisture identification at each site, color identification at each site, or through an algorithm or pre-set of locations or any combination thereof. Wherein said light source having at least one predefined wavelength suitable for treating said vaginal disorders, and said main body (101) and coating (104) are designed to allow said light to pass through and reach vaginal tissue; said light source is designed to emit said light at predefined intervals and intensities suitable for treating said vaginal disorders; and said tether (105) is connected to said main body (101) and is designed to be used for retracting the ILTD outside from the patient's vagina.

In specific embodiments, the above ILTDs further comprise any one of: (i) a camera designed to capture images or movies of the vagina's inner walls; (ii) pH-meter (109) or pH-sensor designed to measure the pH inside the vagina; (iii) a thermometer/temperature-sensor designed to measure the temperature inside the vagina; (iv) moisture sensor; and optionally (v) a data-transmitter designed to transmit data from said camera, pH-meter (109) and thermometer to a remote computing system.

In certain embodiments thereof, the ILTD further comprises one or more active agents—in the main body and/or in the coating-selected from: moisture materials, hormones, photosensitizers, therapeutics, buffer material, and/or biome, or any combination thereof, wherein said device is designed to release said one or more active agents into the vagina; and said light source is designed to emit said light either constantly or at predefined intervals and intensities suitable for treating said vaginal disorders.

Accordingly, in specific embodiments, the present invention provides an intravaginal light-based treatment device (ILTD) (100) for treating patient's vaginal disorders, the device comprises: (a) a main body (101); (b) a light source (102); (c) a power source (103); (d) optionally, a coating (104) over said main body (101); (e) a tether (105); and (f) one or more active agents selected from: moisture materials, hormones, photosensitizers, therapeutics, buffer material, and/or biome, or any combination thereof, wherein said light source is designed to emit either a continuous/constant light or a pulsed light at predefined intervals and intensities suitable for treating said vaginal disorders, having at least one predefined wavelength suitable for treating said vaginal disorders, and said main body (101) and coating (104) are designed to allow said light to pass through and reach vaginal tissue; said device or coating is designed to release said one or more active agents into the vagina; and said tether (105) is connected to said main body (101) and is designed to be used for retracting the ILTD outside from the patient's vagina.

The light source (102) can be electric or chemical, such as a light stick or any other source of light emitting the necessary lumen intensity at a certain wavelength. In a specific embodiment, the light source (102) is LED.

Accordingly, in specific embodiments, the present invention provides an intravaginal light-based treatment device (ILTD) (100) for treating patient's vaginal disorders, the device comprises: (a) a main body (101); (b) a light source (102); (c) a power source (103); (d) optionally, a coating (104) over said main body (101); (e) a tether (105); and (f) one or more active agents selected from: antifungal drugs and antibiotic, or a combination thereof, wherein said light source is designed to emit either a continuous/constant light or a pulsed light at predefined intervals and intensities suitable for treating said vaginal disorders, having at least one predefined wavelength suitable for treating said vaginal disorders, and said main body (101) and coating (104) are designed to allow said light to pass through and reach vaginal tissue; said device or coating is designed to release said one or more active agents into the vagina; and said tether (105) is connected to said main body (101) and is designed to be used for retracting the ILTD outside from the patient's vagina. In specific embodiments thereof, the drug is agisten.

The ILTD of the invention is designed to be used in the vagina. As such, in certain embodiments, it is designed to resemble or have a similar shape/configuration to a typical tampon that can easily be inserted into the vagina for the administration of the light and any other therapeutic therein.

In certain embodiments, the ILTD of the invention is simple and inexpensive to produce in large amounts, and can be manufactured in any size and shape, e.g., to be suited to a variety of vagina's sizes. For instance, it can be in "small", "midi", and "large" sizes. In certain embodiments, the ILTD contains LEDs with an optical lens(s) designed to define the size of the light spot and coverage area.

Non-limiting examples of possible power sources (103) that can be used in the ILTD of the invention are: silver oxide (1.55V) bottom like batteries (without mercury); lithium-ion rechargeable batteries; and AA or AAA batteries-optionally rechargeable. The power source (103) may be integrated within the ILTD's main body (101) such that it resides within the vagina, or be in an external casing (107) connected to the main body (101) via a wire (acting as the tether (105)), such that it resides outside the patient's body. In certain embodiments, e.g., when the power source (103) is a rechargeable battery(s), the ILTD is designed to be re-used, such that the user only needs to clean or replace the coating (104) before each use thereof. Alternatively, e.g., when the power source (103) is external and connected to the main body (101) via a wire, the main body (101) and its contents may be disposable, such that the user only needs to replace the main body (101) and connect it to the same external power source (103). Accordingly, in certain embodiments of any of the ILTD above, the power source (103) is a rechargeable battery(s).

In certain embodiments of any of the ILTD above, the coating (104) is removable, e.g., like a condom that is placed over the main body. In such a case, if the main body (101) is reusable, e.g., by using a power source that can suffice several usages (e.g., up to 5-7 times or more) before depletion, or by using a rechargeable battery, it can be reused by simply replacing the coating (104) with a new one before each use. Moreover, the ability to remove and reinstall the coating provides an ability to replace one type of coating with another (e.g., one coating with a specific active-agent/medicament vs. a coating with a different one), thereby modifying treatment procedures according to need without needing to purchase a new device.

As stated above, the ILTD may contain various sensors, such as pH-sensor, thermometer, etc., for diagnosing vaginal status and/or facilitate treatment and treatment-regimen. In specific embodiments, such sensors are part-of or contained-within the coating (104). For example, identification of a high pH may indicate the presence of a fungi, while a low pH may indicate the presence of a bacteria. Accordingly, after the diagnosis step, a user may choose to use a different coating (104) containing different medications/drugs.

In certain embodiments of any of the ILTD above, the coating (104) is transparent or comprises transparent areas through which light can pass. The term "transparent" as used herein refers to the ability of light at a certain wavelength to pass through the coating (104) and reach the internal walls and surroundings of the vagina.

In certain embodiments of any of the ILTD above, the coating (104) further comprises anti-slip regions (106) designed to assist the ILTD to remain in place, in terms of orientation within the vagina. In specific embodiments, when the coating (104) further comprises therapeutic agent(s), these anti-slip regions (106) may further increase the overall surface area of the coating (104), thereby increasing release rate of such therapeutic agent(s) and thus improve treatment efficiency.

In certain embodiments of any of the ILTD above, the main body (101) is non-circular or comprises protrusions (116) (sec. e.g., FIG. 3B) designed to maintain the ILTD in place after insertion, e.g., into the vagina, thereby facilitating proper placement therein in terms of desired position and orientation, reduce the risk of turning inside, and optionally assist in directing the emitted light in the right and desired direction.

In certain embodiments of any of the ILTD above, the coating (104) is gel-based. In specific embodiments, the gel is biodegradable, bio-absorbable, and allows the release of therapeutics imbedded therewithin or the diffusion of therapeutics therethrough (when they are on or within the main body (101)). In specific embodiments, the gel being used is characterized in that it changes its viscosity at body temperature, meaning that at, e.g., room temperature it is in solid state and at body temperature it changes its viscosity, e.g., liquidizes or becomes less solid thus enabling the release or diffusion of the therapeutics. In certain embodiments, the gel used enables to enhance the treatment and to have a better treatment efficacy.

Non-limiting examples of gel materials that can be used are poly(propylene oxide)-PPO, poly(lactidecoglycolic acid)-PLGA, poly(N-isopropylacrylamide)-PNIPAM, poly(propylene fumerate)-PPF, poly(urethane)-PU, poly(organophosphazene)-POP, poloxamers of the type polyethyleneoxide (PEO)-PPO-PEO, such as poloxamer 68, 88, 98, 108, 124, 127, 188, 237, 338 and 407, stearic acid, poly(acrilicacid), glyceryl stearate, cetearyl alcohol, sodium stearoyl lactylate, hydroxy-lenolin or any combination thereof.

In specific embodiments, the gel material is a hydrophilic biocompatible sustained-release material comprising Pluronic F-127 and Hydroxypropylmethylcellulose (HPMC) (referred to herein as co-polymer F127) in amounts effective to produce a hydrogel composition of sufficiently low viscosity at room temperature and at 37° C. For instance, the gel comprises: 20-30% Pluronic F-127; 0-1.8% PEG-400; 0.1%-0.3% HPMC; and balance water; or 20-30% Pluronic F-127; 0-2.5% PEG-400; 0.05%-0.5% HPMC; and balance water. In specific embodiments, the gel composition further comprises an effective amount of at least one active agent. Other examples and methods of producing materials comprising Pluronic F-127 are described in U.S. Pat. No. 9,040,074, the content of which is incorporated herein by reference.

In certain embodiments, the gel-based coating (104) enables controlled release of active materials from the coating (104), such as therapeutics, steroids, hormones, buffer material that controls the pH, elements controlling the moisture of the vagina, and desensitization agents to ameliorate itching and pain, such as lidocaine. In specific embodiments, this is obtained by controlling the dissolvement/degradation of the gel material. In alternative or added embodiments, this is obtained by the permeability properties of the gel-material. In yet further alternative or added embodiments, the gel-material enables controlling the pH environment within the vagina and/or has bio-resorbing abilities that facilitate healing.

In certain embodiments of any of the ILTD above, the coating (104) is gel-based having a low viscosity at 37° C. The term "low viscosity" as used herein means that the measure of resistance of the gel to deformation is from about 104 to about 108 at 37° C.

In certain embodiments of any of the ILTD above, the coating (104) comprises lysosomes, e.g., liposomes-in gel. One investigated group of bio adhesive polymers are hydrophilic polymers containing numerous hydrogen bond forming groups, such as carbomers, chitosan, sodium aginate, and cellulose derivatives, such as microcrystalline cellulose, methyl cellulose, hydroxyethyl cellulose, hydroxypropyl cellulose, and hydroxypropyl-methyl cellulose. For instance, carbopol gel with acidic buffering capacity and mucoadhesive properties containing polylysine, known as VivaGel®, has been shown to bind to bacteria or viruses and prevents them from affecting the organism's cells.

In certain embodiments, the ILTD according to any of the embodiments above further comprises any one of: (i) a camera designed to capture images or movies of the vagina's inner walls; (ii) pH-meter (109) or pH-sensor designed to measure the pH inside the vagina; (iii) a thermometer/temperature-sensor designed to measure the temperature inside the vagina; (iv) moisture sensor; and optionally (v) a data-transmitter designed to transmit data from said camera, pH-meter (109) and thermometer to a remote computing system.

In specific embodiments, the ILTD according to any of the embodiments above further comprises a data-transmitter and any one of: (i) a camera designed to capture images of the vagina's inner walls; (ii) pH-meter (109) designed to measure the pH inside the vagina; (iii) a thermometer/temperature-sensor designed to measure the temperature inside the vagina; and (iv) moisture sensor, wherein the data-transmitter is designed to transmit data from the camera, the pH-meter (109) and the thermometer to a remote computing system, such as a smartphone or laptop.

Figure 12A:
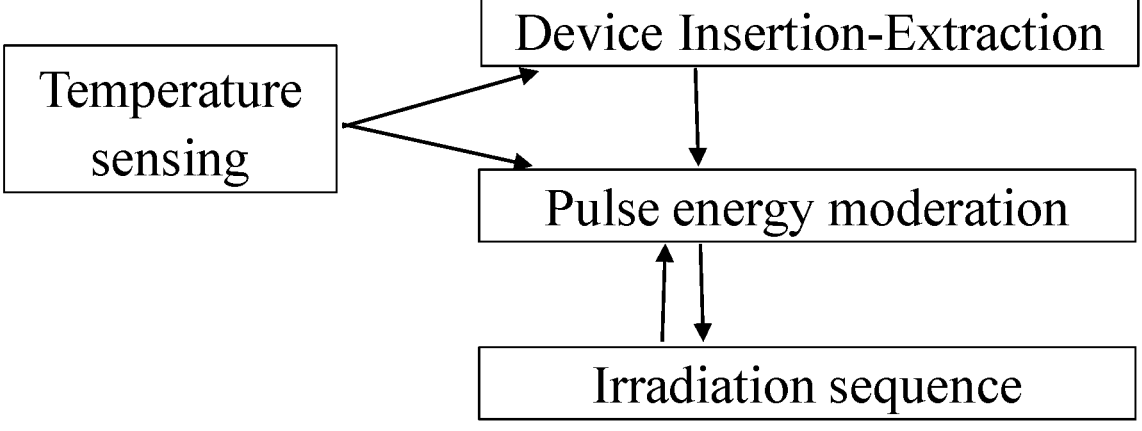
FIGS. 12A-12B are diagrams illustrating an operation algorithm of the ILTD, according to some embodiments of the invention.
Figure 12B:
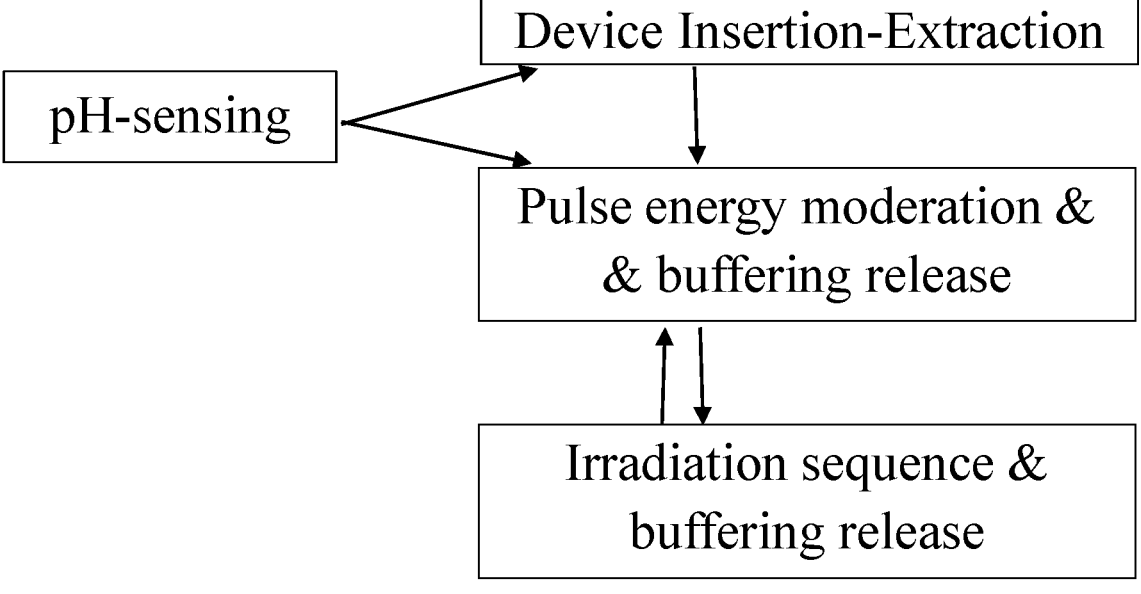

In certain embodiments, when the ILTD of the invention comprises a pH-sensor or pH-meter (109), said pH-sensor is designed to measure the pH in the vagina and initiate an action, such as: sending out an alert (to the user or a caretaker) once it identifies that the pH has reached a certain predefined level, which is indicative of a condition that needs attention. Alternatively, or in addition, once the ILTD identifies that the pH has reached a certain predefined level it can initiate the release of a buffer-material/buffering-agent embedded within, e.g., the main body (101) or the coating (104), to bring the pH back to a normal or desired level, e.g., of 4 or 4.5. FIG. 12B illustrates an algorithm according to which the ILTD automatically modify treatment, e.g., turns the light source on and off or release buffer material, according to the measured pH.

In certain embodiments, the ILTD according to any of the embodiments above further comprises or is associated-with a computing system comprising a processor and a memory communicatively coupled to the processor, the memory comprising computer-readable instructions that when executed by the processor cause the computing system to implement a method of treating patient's vaginal disorders, the method comprising any combination of the following steps: (i) activating and deactivating said light source (102)—either constantly or periodically (pulsing) at the same or different wavelengths and intensities; (ii) releasing one or more active agents (from the main body or coating), such as moisture materials, hormones, photosensitizers, therapeutics, buffer material and/or biome, into the vagina; (iii) measuring pH, temperature and moisture in the vagina, and optionally releasing suitable active agents to ameliorate the pH or moisture, and/or to adjust the light intensity or turn it off to reduce temperature; (iv) stop illumination in a certain location/direction and alter the illumination to a different site/area; (v) change illumination regimen; (vi) detecting bleeding, and optionally releasing suitable active agents to ameliorate the bleeding and/or sending an alert to the user; and (vii) taking images/video movie.

The term "moisture material" as used herein refers to any substance that can cause an alteration in the vagina's internal moisture condition-either increase or decrease it. Such material can be moisturizers that add moisture, hydrates that absorb water and thus reduce surrounding's moisture, or materials that initiate physiological reactions and pathways that lead to an increase or decrease in the overall moisture within the vagina.

Accordingly, in certain embodiments of the ILTD according to any of the embodiments above, the main body (101) comprises or the coating (104) comprises or is coated-with: (i) buffer material designed to be released into the vagina to adjust pH inside the vagina; (ii) one or more therapeutics, such as anti-inflammatory, anti-fungal, anti-viral, and anti-bacterial drugs, or steroids and hormones and anti-irritation drugs, designed to be released into the vagina according to need; (iii) one or more photosensitizers, designed to be activated by light emitted from said light source (102); or (iv) dimethyl sulfoxide (DMSO).

In specific embodiments thereof, the therapeutics are designed to be released automatically (i) by diffusing therethrough; (ii) due to dissolving of the coating's material; (iii) according to environment pH and/or temperature; or (iv) according to instructions received from a computing system according to a predefined treatment regimen.

In certain embodiments, the coating (104) comprises or is coated-with a buffer material/buffering agent designed to be released into the vagina to adjust pH inside the vagina. For example, the buffer material may be released into the vagina to adjust the pH to about 3.5, 4, 4.5 or 5. The buffer material is designed to be released either automatically according to pH level inside the vagina, e.g., due to pH-sensitive coating material or gel-composition, or electronically via a pH-sensor that measures the pH in the vagina and according thereto enables the computing system to determine whether to release the buffer material or not, and in what amount and rate.

In certain embodiments, the ILTD according to any of the embodiments above is designed to maintain a desired pH in the vagina, such as a pH from about 2 to about 7; from about 2 to about 6; from about 2 to about 5; from about 2 to about 4.5; from about 2 to about 4; or from about 2.5 to about 4.5.

In certain embodiments, the ILTD according to any of the embodiments above further comprises an active agent(s) designed to be released into the vagina. In specific embodiments, the active agent(s) is selected from: moisture materials, hormones, photosensitizers, therapeutics, buffer material, and/or biome/probiotics.

In certain embodiments of the ILTD according to any of the embodiments above, the coating (104) comprises or is coated-with one or more such active agents/therapeutics, such as anti-inflammatory, anti-fungal, anti-viral, and anti-bacterial drugs, or steroids and hormones, or elements controlling the moisture of the vagina, designed to be released into the vagina according to need.

Non-limiting examples of active agents/therapeutics are: Antifungal agents: clotrimazole, fluconazole, metronidazole, imidazole, triazole, pyrazole, tinidazole, colistin, butoconazole, miconazole, terconazole, and tioconazole; Antibiotics: clindamycin, and nystatin. Non-limiting examples of hormones are: estrogens and progestogens; elements controlling the moisture of the vagina; anti-irritation or desensitization drugs, such as lidocaine; etc. In specific embodiments, the active agents/therapeutics are designed to be released automatically from the coating (104) by diffusing therethrough. In alternative specific embodiments, the active agents/therapeutics are designed to be released automatically from the coating (104) due to dissolving of the coating's material or a coating of the coating (104). In further alternative specific embodiments, the active agents/therapeutics are designed to be released automatically from the coating (104) according to environment pH and/or temperature. In yet further alternative specific embodiments, the active agents/therapeutics are designed to be released according to instructions received from a computing system according to a predefined treatment regimen.

Compounds that are useful are those that kill or substantially inhibit the growth of infectious microorganisms of interest. Non-limiting examples of active agents designed to kill and/or inhibit the growth of various microorganisms include variety of glycerol-based compounds, such as fatty acid esters of glycerol in which the alcohol group on one, or both, of the terminal carbon atoms of glycerol, the alcohol group on only the middle carbon atom, the alcohol groups on the middle carbon atom and one of the terminal carbon atoms, or the alcohol groups on all three carbon atoms are esterified with fatty acids. The fatty acids can be 10, 11, 12, 13, or 14 carbon linear alkyl fatty acid esters and can be present in the molecule in any combination. In addition, instead of being linked to the glycerol backbone by ester linkages, 10, 11, 12, 13, or 14 carbon linear alkyl chains can be linked to it by ether linkages. Thus, examples of useful compounds include glycerol ester-linked to monolaurate, glycerol dilaurate, glycerol monocaprylate, glycerol monocaprate, glycerol monomyristate, and glycerol monopalmitate. Additional compounds useful in the invention include, e.g., phosphatidyl choline and phosphatidyl ethanolamine; and sphingolipids such as ceramides.

As used herein, the term "substantially inhibit the growth" means at least two-fold (e.g., at least three-; four-; five-; six-; seven-; eight-; nine-; ten-; 25-; 50-; 100-; 1,000-, or greater) inhibition of growth. For in-vivo methods, the killing or substantial inhibition of growth will generally be at a concentration of the inhibitory compound that is not fatally toxic to the host organism or the surrounding tissues.

The dosages of the active agents, such as killing and inhibitory compounds, as well as the dosages of any other supplementary agents to be used, depend on the choice of the route of administration; the nature of the formulation; the nature of the patient's illness; the subject's size, weight, surface area, age, and sex; other drugs being administered; and the judgment of the attending physician. Suitable dosages are generally in the range of 0.0001-100.0 mg/kg. Wide variations in the needed dosage are to be expected in view of the variety of compounds and supplementary agents available and the differing efficiencies of various routes of administration. For example, oral administration would be expected to require higher dosages than administration by i.v. injection. Variations in these dosage levels can be adjusted using standard empirical routines for optimization as is well understood in the art. Administrations of compounds and/or supplementary agents can be single or multiple (e.g., 2-, 3-, 4-, 6-, 8-, 10-, 20-, 50-, 100-, 150-, or more fold). Encapsulation of the compounds and/or supplementary agents in suitable delivery vehicles (e.g., polymeric microparticles or implantable devices) may increase the efficiency of delivery.

Photodynamic therapy (PDT) is a form of phototherapy involving light and a photosensitizing chemical substance, used in conjunction with molecular oxygen to elicit cell death (phototoxicity). PDT is popularly used in various treatments, such as for treating acne, psoriasis, atherosclerosis, anti-viral treatments, anti-cancerous treatments. PDT is considered as both minimally invasive and minimally toxic. Photodynamic therapy's advantages lessen the need for surgery and lengthy medication therapy.

Many photosensitizers for PDT exist. They divide into porphyrins, chlorins and dyes. Non-limiting examples of photosensitizers known in the art are methylene blue, toluidine blue O, and rose Bengal, aminolevulinic acid (ALA), silicon phthalocyanine Pc 4, m-tetrahydroxyphenylchlorin (mTHPC), mono-L-aspartyl chlorin c6 (NPe6), Allumera, Photofrin, Visudyne, Levulan, Foscan, Metvix, Hexvix, Cysview, Laserphyrin, Antrin, Photochlor, Photosens, Photrex, Lumacan, Cevira, Visonac, BF-200 ALA, Amphinex, and Azadipyrromethenes.

Various photosensitizers and their effect on *Candida auris* have been studied, as seen, e.g., in Bapat et al., Front. Cell. Infect. Microbiol., 2021, the content of which is incorporated herein by reference.

Accordingly, in certain embodiments, the ILTD according to any of the embodiments above further comprises photosensitizers designed to be released into the vagina and activated thereafter by light emitted from the light source (102) of the ILTD. In specific embodiments, the photosensitizers are within the coating (104). Accordingly, in specific embodiments, the coating (104) comprises or is coated-with one or more photosensitizers, designed to be released into the vagina and be activated by light emitted from the light source (102) of the ILTD.

Dimethyl sulfoxide (DMSO) is an organosulfur compound of the formula $(CH_3)_2SO$, and is used mainly as a polar aprotic solvent that dissolves both polar and nonpolar compounds and is miscible in a wide range of organic solvents as well as water.

DMSO is well known in the medicine field due to its ability to penetrate the skin and other membranes without damaging them while carrying other compounds into a biological system thereby increasing transdermal drug delivery. DMSO has been shown to enhance transformation of prokaryotes and eukaryotes, and is used as an anti-inflammatory agent and an antioxidant, and is frequently compounded with antifungal medications, enabling them to penetrate not just the skin but also nails. DMSO's effect may be enhanced with the addition of EDTA.

DMSO can be used as a pre-treatment before the treatment of the pathogen and/or as part of a gel-form substance, e.g., by using DMSO as a stock suspension for various drugs, such as antifungal drugs. Examples of antifungal drugs are fluconazole, voriconazole, itraconazole, and amphotericin B. The release of any drug from a poloxamer gel depends on the environment. The release is controlled by dissolution of the gel if it is placed in an aqueous environment (as in vaginal administration), while diffusion is the main mechanism if the gel is confined by a membrane, as in transdermal applications.

Accordingly, in certain embodiments, the ILTD according to any of the embodiments above further comprises DMSO. In specific embodiments, the coating (104) comprises or is coated-with DMSO.

In certain embodiments, the ILTD according to any of the embodiments above, is further designed to modify the vagina's biome. Such modification can be due to pH-, moisture- and temperature-adjustments, or administration of flora-affecting medications, as described herein, and/or by introducing a specific biome into the vagina, wherein the specific biome is obtained from a donor or is an autologous donation. In specific embodiments, the introduction of a specific biome into the vagina can be done after receiving a sample from the donor (or self) and proliferating the desired biome, inserting the proliferated biome into the ILTD, e.g., into the main body (101) or into the coating (104), in any suitable manner, such as in a suspension, lyophilized or in vesicles. Once inside the vagina, the ILTD can release the desired biome either automatically or according to specific instructions received from an external computing system. Such modification of the biome and flora of the vagina can facilitate healing and improve the vagina's health, and may assist in preventing recurrence of the treated condition or disease.

The coating (104) according to any of the embodiments above can be prepared in any suitable way, such as molding, press-molding, 3-D printing, etc. In certain embodiments, the coating is prepared individually from the main body (101) and is designed to be mounted thereon. In alternative embodiments, the coating is fabricated directly onto the main body (101), e.g., by spraying thereon or dipping the main body (101) in the coating's material in liquid state. Also, it may include additives designed to provide desired characteristics, such as low viscosity at 37° C. and higher viscosity at room temperature, dissolvability under certain pH and/or temperature, stability, or any or desired characteristic(s).

Waste heat is heat that is produced as a byproduct by a process that uses energy as a fundamental result of the laws of thermodynamics. One such process is generation of light. Usually, body heat is around 37° C., and preferably below 39° C. Accordingly, it is advisable that a light-emitting device within the vagina will not cause an increase in the vagina's temperature above 39° C. Accordingly, the ILTD according to any of the embodiments above is designed to prevent overheating of the vagina over 39° C. or any other desired preset temperature (such as 38.5° C., 38° C., 37.5° C. and 37° C.). This can be done by any suitable way, such as conducting heat generated by the ILTD/light source (102) away from the ILTD and the vagina and/or by controlling the light source's activity.

In certain embodiments, the controlling of the temperature within the patient's vagina/cavity is done by a proportional-integral-derivative (PID) algorithm by varying duty cycles of the pulses.

Accordingly, in certain embodiments of the ILTD according to any of the embodiments above, the tether (105) is a heat-conduit designed to remove excess heat generated by said ILTD (e.g. by the light source) outside from the vagina thereby preventing overheating of the vagina, e.g., to a temperature over 39° C. Accordingly, in certain embodiments, the tether (105) contains a cupper braided wire to conduct heat out of the patient's body. Alternatively, or in addition, the ILTD according to any of the embodiments above further comprises a temperature sensor or thermometer designed to measure the temperature in the vagina, such that if the temperature exceeds a predefined temperature, the light source (102) is turned off in order to stop the heat generation and cool down the ILTD. The turning-off of the light source (102) may be directly through the thermometer (e.g., due to physical deformation thereof and disconnection of power conduits) or via a computing system that receives temperature data from said temperature sensor or thermometer and controls the activation of the light source (102), such that when it is noted that the temperature has passed a predefined threshold, the light energy is reduced by adjusting the duty cycle pulses, thereby eliminating heat generation by said light source, and subsequently reducing the temperature (i.e. cooling), see, e.g., illustrated in FIG. 12A, in which the algorithm of the ILTD automatically turns the light source on and off according to the measured temperature. If the temperature still exceeds a predefined threshold, the light source may be turned off completely. For instance, when the ILTD senses that the temperature is below 36° C., it will turn the light on, and when it senses that the temperature has passed 38.5° C., it will turn the lights off. In alternative or added embodiments, the light source in front of the heated zone/tissue, may be shut down, while other LEDs in front of other zones, that remain or are cool is turned on or remain on. Temperature sensor may be thermocouple, RTD, or other type of commonly use temperature sensors.

The ILTD according to the invention is designed to treat various conditions and diseases using light. Light has been shown to have a therapeutic effect on various diseases and pathogens, and several studies have been made to analyze the effect of various wavelengths and intensities on different pathogens. For instance, US 2016/0059034, the content of which is incorporated herein by reference, has shown that blue- and red-lights wavelengths aids in *candida* therapy in the vagina.

Accordingly, in certain embodiments of the ILTD according to any of the embodiments above, the light source (102) of the ILTD is designed to emit light with a wavelength in a therapeutic zone. For instance, the light source (102) emits a non-UV germicidal light with a wavelength ranging between a blue-light wavelength and/or a red-light wavelength or a violet-light wavelength. In specific embodiments, the light source (102) emits light in the range of about 405 nm to about 470 nm. In alternative or added specific embodiments, the light source (102) emits light in the range of about 620 nm to about 750 nm. In yet another alternative or added specific embodiments, the light source (102) emits light in the range of about 380 nm to about 450 nm. The emitted light is designed to kill or limit propagation of various pathogens such as bacteria, viruses and fungus.

In certain embodiments of the ILTD according to any of the embodiments above, the light source (102) is designed to emit: (i) light at variable wavelengths and intensities according to a predefined treatment regimen; (ii) red-, green-, or blue-visible light, or any combination thereof; (iii) infrared (IR) and ultraviolet (UV) light, or both; or (iv) laser light, or any combination thereof.

The term "visible blue-light" as used herein refer to light of wavelength of from about 384 nm to about 500 nm. The term "visible green-light" as used herein refer to light of wavelength of from about 500 nm to about 600 nm. The term "visible red-light" as used herein refer to light of wavelength of from about 600 nm to about 700 nm. Accordingly, in specific embodiments, the ILTD of the invention is designed to emit light at a wavelength of 384 nm, 405 nm, 415 nm or 455 nm, or any combination thereof.

Light waves not only have length, but also have an amplitude, wherein the greater the amplitude is, the brighter/stronger the light is. For instance, a light at 550 nm will appear green, either dim at low intensity or bright at a high intensity; however, the color remains the same. The greater the intensity, the more energy is being transmitted. Accordingly, the ILTD of the invention may emit light at growing or reducing intensity throughout time. Changing of the light intensity may have a therapeutic effect and improve tissue healing as well as improve eradication of an infection, such as fungi, virus or bacteria, or affect the photosensitize regimen if and when used. For instance, the intensity of the emitted light may be increased after X hours for a fixed period, reduced back to the original intensity, and so forth throughout the day/usage duration.

In certain embodiments of the ILTD according to any of the embodiments above, the light source (102) is designed to emit light: (i) constantly at the same wavelength and intensity; (ii) at different wavelengths and/or intensities; and/or (iii) pulsed light or in intervals, wherein in each session of illumination, the light is emitted either in the same wavelength and intensity or at a different wavelength and intensity, or any combination of light emissions scenarios.

In a non-limiting example of constant wavelength and intensity, the ILTD can emit constant 20 mW/cm$^2$ of light for 10 minutes at a wavelength of 405 nm. In another non-limiting example, the ILTD can switch between 10 mW/cm$^2$, at a wavelength of 405 nm and 20 mW/cm$^2$ at a wavelength of 450 nm. In another non-limiting example, the ILTD can be set to emit pulses of 10 mSec, with duty cycle of 50% at wavelength of 405 nm during a 1-hour session and emit pulses of 10 mSec, with duty cycle of 20% at a wavelength of 450 nm at the next 2-hour illumination session.

The ILTD according to any of the embodiments above can emit a "single-color" light at a certain wavelength range, or multiple single-colors lights, each at a different wavelength range either simultaneously or interchangeable according to a treatment plan. The light emission may be continuous, i.e., the light will be constantly on, or intermediate, i.e., the light will be turned on and off (i.e., duration of light pulsed can be controlled) according to a treatment plan, each time turning the same or different light-color, with the same or different intensity. The Activation of the light may be prior to the insertion of the ILTD into the vagina, e.g., by turning an activation switch immediately before insertion, or after insertion, e.g., using a remote control or a smartphone with a dedicated application. For instance, a user may turn the ILTD on and insert it into the vagina; then, the light may be turned on continuously until the ILTD is removed and turned off.

The duration-, intensity-, and a pulsed light, have all been shown to have various therapeutic effects. For instance, using light pulses has been shown to induce stress on targeted pathogens, such as bacteria or yeast, which reduces their ability to survive and multiply. Accordingly, in alternative embodiments, after inserting the ILTD, the light source (102) is turned on and off (i.e., pulsed light) according to a predefined treatment sequence.

In a non-limiting example the ILTD is set to emit a first train of light pulses with power density of 12 mW/cm$^2$ and a duty cycle of 30%, at a wavelength of 405 nm for 1 hour, then cease illumination for an interval of 3 hours and then repeat the first train of pulses again, the cease illumination for an interval of 2 hours and then repeat the first train of pulses again—for a total of 3 hours of illumination with 12 mW/cm$^2$ pulses with 30% duty cycle, over a span of 7 hours.

In certain embodiments, the ILTD comprises a temperature measurement means and/or an electrical conductance means. Accordingly, the activation and operation of the ILTD is designed to start when the computing system (or control circuit) senses an increase in the device's temperature (or the surrounding temperature) that corresponds to the insertion of the ILTD into the patient's vagina and/or an increase in conduction that may be affected by the moisture of the vaginal tissue. In addition, the ILTD stops its operation when either its power source is depleted or when the computing system (or control circuit) senses a decrease in the device's temperature and/or decrease in conduction that corresponds to removal of the device from the vagina.

In another alternative, the ILTD is emitted only after insertion into the vagina, and the light can be turned on continuously or interchangeably in pulses or continuously according to a predefined treatment sequence/plan. In any of these examples, the emitted light can be of the same wavelength and intensity throughout the entire time the ILTD is in the vagina, or may be altered—in color and/or intensity according to a predefined treatment plan.

Figure 13:
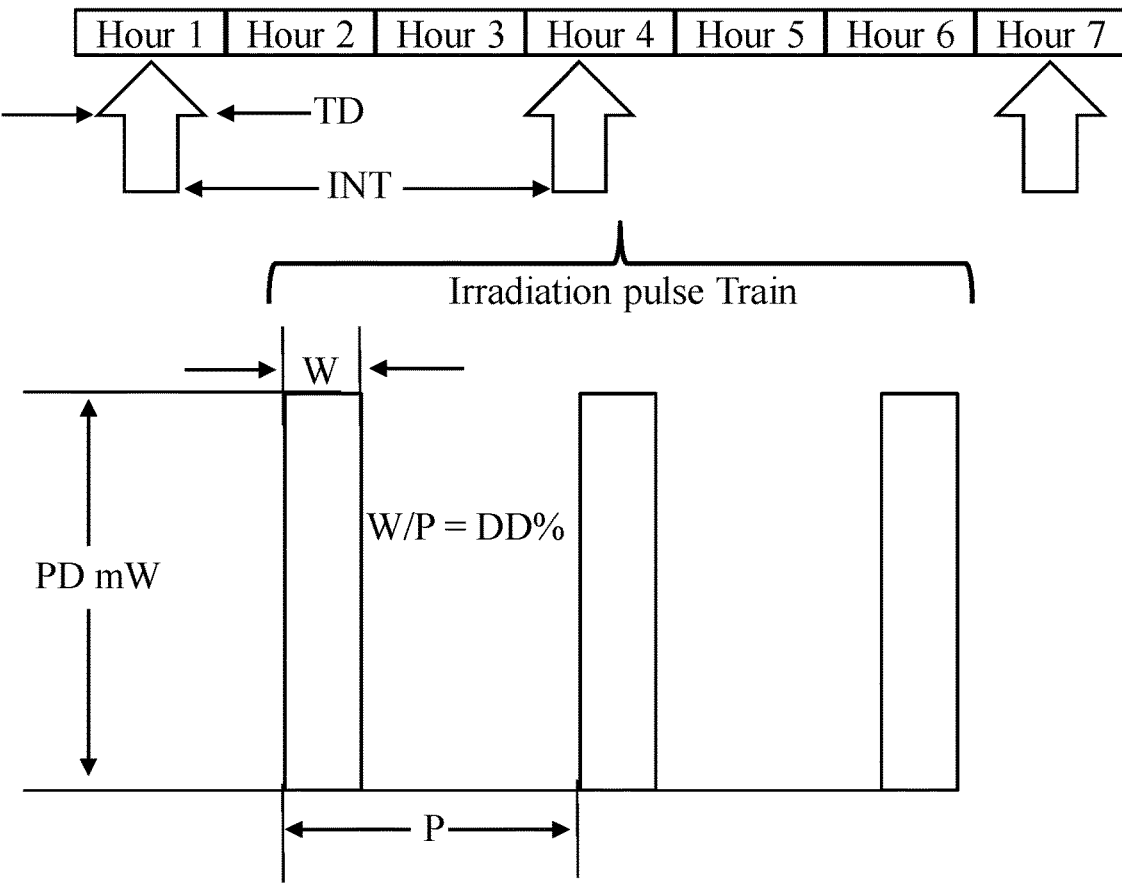
FIG. 13 is an illustration of one possible irradiation sequence.

FIG. 13 depicts an irradiation regimen of the ILTD according to specific embodiments of the invention. As illustrated, a regimen consists of several pulse trains, where light pulses are characterized by their pulse width, that is defined as the duration between pulse start (ON state) and end (OFF state), and duty cycle, that is defined as the percentage of ON state time during the duration between two pulse start points. The light source (LEDs) is lit individually with the same pulse width and duty cycle but with staggered start time, such that the total number of LEDs that are at ON state at any time is minimal. The irradiation parameters are set to minimize heat buildup of the irradiated tissue, by leaving sufficient non-lit time at each area for heat dissipation by the vaginal blood vessels during that time. The train of pulses continues for a planned Train Duration and is repeated after an Interval period that is set according to the targeted pathogen life cycle and to maximize the disinfection effect.

The ILTD according to any of the embodiments above emits light according to predefined sequences/regimes (duty cycles) intend to treat and ameliorate the vaginal disorder. In specific embodiments, the idea of the duty cycles is to optimize the killing effect, which depends on the intensity rather than on the total dosage. For instance, short-term and low intensity blue-light radiation causes formation of free radicals, which the fungus has sufficient time to recover. However, when short-pulses with high intensity irradiation are used, larger number of radicals are formed, which can lead to fungus death. Non-limiting examples of duty cycle patterns are: (i) 50 milliseconds on & 50 milliseconds off; (ii) 100 milliseconds on & 50 milliseconds off; (iii) 150 milliseconds on & 50 milliseconds off; (iv) 50 milliseconds on & 100 milliseconds off; (v) above 50 milliseconds on & above 50 milliseconds off; (vi) above 100 milliseconds on & about 50 milliseconds off; (vii) above 50 milliseconds on & below 50 milliseconds off; or any other suitable combination. In certain embodiments, the duty cycles may be symmetric (i.e., repeating identically) or asymmetric. Notably, when the light is turned-off, any heating of the vaginal tissue due to light irradiation, which is an undesired side-effect, is dissipated by the vaginal blood flow, thereby reducing the risk of overheating the vagina/cavity tissue and thus facilitates healing and reduces the risk of damage to the nearby patient's tissue.

The ILTD according to the invention can be designed in any shape and configurations. For instance, in certain embodiments, the main body (101) holds only the light source (102) while the power source (103) is placed, e.g., in a remote/external casing (107). In alternative embodiments, the main body (101) holds both the light source (102) and the power source (103). In other alternative embodiments, the main body (101) does not hold either the light source (102) nor the power source (103), and both are placed, e.g., in a remote/external casing (107) and delivered into the main body located in the vagina through suitable cables/wires, such as a light-guide or an optic-fiber.

In certain embodiments of the ILTD according to any of the embodiments above, the main body (101) further comprises light diffusers designed to spread light emitted from the light source (102) in all directions, e.g., 360° perpendicular to the ILTD, thereby enabling emitting light all around while using limited number of light-emitting sources/points. For instance, one, two, three or more single LEDs can be used to emit light in a 360° perpendicular to the ILTD. Alternatively, or in addition, the light source (102) comprises multiple light points spread along the main body (101) and designed to emit light in all directions. For instance, a single line of LEDs along the main body (101) together with light diffusers can be used to obtain a 360° light spread, or 3 or 4 lines of LEDs along the main body (101) can be used to obtain the same effect without such light diffusers.

The ILTD according to invention can be designed to be used only once, i.e., for a single use. In such a case it may be discarded after each use. Alternatively, the ILTD can be designed for multiple uses, in which case it can have various combinations. For instance, it may comprise a rechargeable battery as the power source (103) to provide long lasting power throughout the ILTD's life span. Alternatively, or in addition, the main body (101) with all its inner components may be reusable, whereas only the coating (104) is disposable, in which case the user is required to remove an old/used coating (104) and mount a new one on the main body (101) before each use. This enables to reduce costs and minimize waste. For example, the coating may be a condom-like coating that is transparent to the emitted light and covered with an active agent and a gel material designed to hold the active agent, maintain a desired viscosity and lubrication, and control the release rate thereof. Another alternative is that the main body (101) is hollow, and the power source (103) as well as the light source (102) are in a remote casing (107) and are connected, e.g., via an optic-fiber or any other light guide. In such a case, the main body (101) itself can be disposable and the user only needs to detach it from the remote casing (107)/optic-fiber and attach a new main body before each use. Notably, even when the main body is empty as detailed above, it might still be re-usable, again, by using a disposable coating (104) as detailed hereinabove.

In certain embodiments, the ILTD according to any of the embodiments above further comprises a camera. The camera is intended to capture images or movie(s) of the vagina's inner walls and transmit same to a remote computing system, such as a computer, laptop, and smartphone. In specific embodiment, the computing system comprises an artificial intelligence software designed to identify deficiencies in the vagina's inner walls caused due to various disorders, such as pH imbalance, infections or other. Contrary to a normal camera that forms an image using visible light, namely in the 400-700 nm range of the visible light, IR-camera uses wavelength from about 1,000 nm to about 14,000 nm. Accordingly, in specific embodiments, the light source (102) is designed to emit infrared (IR) light, and the camera is an IR-camera or thermographic-camera designed to create images using IR radiation.

Another option for emitting light is chemical light, such as used in stick-lights/glowsticks. Accordingly, in certain embodiments of the ILTD according to the invention, the light source (102) is a chemical, non-electric, light source. In specific embodiments, the power source (103) is absent, and activation of the light source (102) is done by mixing two or more reagents together immediately prior to use of the ILTD. In alternative specific embodiments, the activation of the light source (102) is done electronically by mixing two or more reagents together according to a predefined order. In such a case, a computing system may control the release and mixing of the reagents within the main body, thereby enabling generation of light in various colors/wavelengths (or a single color/wavelength can be used).

In certain embodiments of the ILTD according to any of the embodiments above, the vaginal disorders are selected from: (i) infections, such as bacterial-viral- or fungal-infections; (ii) pH disorders, which are either due to an infection or not, in which case they are known to be a leading cause to such infections; and (iii) any other type of disorder that does not fall under the above two categories.

In certain embodiments, the ILTD according to any of the embodiments above further comprises an activation switch, which can be on the main body (101), in a remote/external casing (107), or in a remote smartphone (i.e., electronic switch).

In certain embodiments, the ILTD according to any of the embodiments above does not comprise an activation switch, and activation of the ILTD occurs based on identification that it has been inserted in the vagina, e.g., by identifying that the temperature as exceeded 36° C. and/or according to moisture level. Accordingly, turning the ILTD off is automatically once it is removed from the vagina.

Since the main body (101) and coating (104) are designed to be inserted into the vagina, they are, both or just the coating (104), made of medical grade material designed to prevent irritation and damage to the vagina's tissues. In addition, the main body (101) is designed to be sealed to avoid a flow of vaginal fluid therein and into the ILTD.

In certain embodiments, the ILTD according to any of the embodiments above can be in any size and shape. For instance, it can be manufactured in 3 different lengths designed to fit different ages: small (e.g., 2.5 cm in length);

medium (5 cm in length); and large (7 cm in length). The diameter of the ILTD can be, e.g., from about 0.8 cm to about 1.5 cm, such as 1 cm.

As noted above, the ILTD according to the invention can be manufactured in any desired configuration. Accordingly, in specific embodiments, the ILTD according to any of the embodiments above is disposable, and the main body (101) and coating (104) constitute a single unit holding the light source (102) and the power source (103). In alternative specific embodiments, the ILTD is disposable, the light source (102) is non-electric and the power source (103) is absent, and optionally the main body (101), the coating (104) and the tether (105) constitute a single unit. In other alternative specific embodiments, the ILTD is reusable, namely by reusing the main body (101) and replacing the coating (104) after each use, and optionally the power source is inside the main body (101) or is in an external casing (107). In yet other alternative specific embodiments, the light source (102) is inside the main body (101) and the power source (103) is in an external casing (107), and the tether (105) is used to transfer power from the power source (103) to the light source (102). In yet other alternative specific embodiments, the main body (101) is hollow/empty and the light source (102) and the power source (103) are both in an external casing (107), and the tether (105) acts as an optic-fiber/light-guide and is used to transfer light from said external casing (107) to said main body (101). In specific embodiments thereof, the main body (101) is disposable and disconnectedly connected to the tether (105).

In certain embodiments, the ILTD according to any of the embodiments above is designed for use in treating patient's vaginal disorders. In alternative or added embodiments, the ILTD according to any of the embodiments above is designed for diagnosing various disorders or conditions of a patient's vagina. In specific embodiments thereof, the treatment or diagnosing is of fungal-, bacterial- or viral-infection. In further specific embodiments: the fungal infection is an infection caused by yeast, such as *Candida albicans, Candida tropicalis* and *Candida krusei*; and the bacterial infection is an infection caused by Gardnerel. In specific embodiments, the disorder is caused by gonorrhea, *Chlamydia, mycoplasma*, herpes, *Campylobacter* and *Trichomonas vaginalis*.

In certain embodiments, the ILTD according to any of the embodiments above is capable of monitoring the vagina's health condition, e.g., by measuring pH, temperature and/or moisture using suitable sensors, and/or by monitoring or identifying the presence of various pathogens, and optionally also diagnosing the type of pathogen or condition, and subsequently adjust/change the treatment protocol according to the identified, e.g., change the light intensity, wavelength, or other parameter relating to the light, and/or adjust the amount, rate and/or type of the released active agent(s), or any other adjustment, or combination thereof.

In certain embodiments, the ILTD of the invention is a diagnosing-ILTD that enables to monitor the vagina's health condition by measuring pH, temperature and/or moisture using suitable sensors, and/or by monitoring or identifying the presence of various pathogens, such as viral, fungal or bacterial pathogens, using any suitable means, such as a camera, an IR-camera, pH-meter (109), pathogen-specific sensors, etc. The diagnosing-ILTD is designed to send all the collected data to a remote computing system, such as a laptop or smartphone, which is equipped with a dedicated software designed to analyze pictures and other received data and determine whether a pathological condition is present or not. The data is transmitted either via a wire or wirelessly, e.g., using WiFi or Bluetooth, optionally via a breaded antenna breaded with the tether (105).

In certain embodiments, the diagnosing-ILTD of the invention is used for diagnosing the cause for the vaginal disorder/illness, e.g., due a bacterial- or fungal-infection, like *candida*. In specific embodiments, the diagnosis is carried out based on the various measured parameters, such as the initial pH, temperature and moisture. Following diagnosis, the ILTD (or the associated computer) may recommend a specific treatment regimen and/or the use of a specific coating, e.g., use a coating comprising anti-fungal agent(s) for treating a fungal infection, and use a coating comprising antibiotics when the infection is bacterial. It may also provide or initiate specific illumination regimen that is optimized for the targeted pathogen.

In another aspect, the present invention provides kits for treating patient's vaginal disorders, the kits comprising one or more intravaginal light-based treatment device (ILTD) (100) for treating patient's vaginal disorders, the ILTD comprises: (a) a main body (101); (b) a light source (102); (c) a power source (103); (d) optionally, a coating (104) over said main body (101); and (e) a tether (105), wherein said light source is designed to emit pulsed- or continuous-light having at least one predefined wavelength suitable for treating said vaginal disorders, and said main body (101) and coating (104) are designed to allow said light to pass through and reach vaginal tissue; said light source is designed to emit said light at predefined intervals and intensities suitable for treating said vaginal disorders; and said tether (105) is connected to said main body (101) and is designed to be used for retracting the ILTD outside from the patient's vagina.

In another aspect, the present invention provides kits for treating patient's vaginal disorders, the kits comprising ILTD (100) for treating patient's vaginal disorders, the ILTD comprises: (a) a main body (101); (b) a light source (102); (c) a power source (103); (d) optionally, a coating (104) over said main body (101); (e) a tether (105); and (f) one or more active agents selected from: moisture materials, hormones, photosensitizers, therapeutics, buffer material, and/or biome, or any combination thereof, wherein said light source is designed to emit either a continuous/constant light or a pulsed light at predefined intervals and intensities suitable for treating said vaginal disorders, having at least one predefined wavelength suitable for treating said vaginal disorders, and said main body (101) and coating (104) are designed to allow said light to pass through and reach vaginal tissue; said device or coating is designed to release said one or more active agents into the vagina; and said tether (105) is connected to said main body (101) and is designed to be used for retracting the ILTD outside from the patient's vagina.

In specific embodiments, the above kits comprise two or more ILTDs and/or tow or more coatings.

In yet another aspect, the present invention provides kits for monitoring and diagnosing a patient's vaginal health condition, the kits comprising one or more ILTDs according to any of the embodiments above. In specific embodiments, the kits comprise two or more ILTDs.

In certain embodiments, the present invention provides vaginal diagnosing kits comprising: (a) an intravaginal light-based diagnosing device as defined hereinabove, optionally with coatings (104) designed to be used by said device. In specific embodiments of such kits, the device comprises an external casing (107) with a power source (103) and a light source (102) that is designed to be re-usable and before each use the user replaces the main body (101) and/or its coating (104). Optionally, after all main bodies (101) (and coatings) in the kit are used, the device (i.e., the external casing (107)) is also discarded.

In certain embodiments, the present invention provides vaginal diagnosing and treatment kits comprising: (a) an intravaginal light-based treatment device (ILTD) according to any of the embodiments above, with one or more different (or same) coatings (104) designed to be used by said ILTD. In specific embodiments of such kits, the ILTD comprises an external casing (107) with a power source (103) and a light source (102) that is designed to be re-usable and before each use the user replaces the main body (101) and/or its coating (104). In such kits, the main body (101) is used both for diagnosing and for treatment. Accordingly, the ILTD may be first used for diagnosing, i.e., used with a coating that does not include any drugs, or without a coating. After the ILTD gathers information, e.g., temperature, moisture, pH, images, etc., and the reason for the disorder is determined, the ILTD is extracted, and a suitable coating, with suitable drug (e.g., anti-fungal, antibiotic, etc.) is placed thereon to commence treatment after re-insertion thereon into the vagina. Optionally, after all main bodies (101) (and coatings) in the kit are used, the device (i.e., the external casing (107)) is also discarded.

In certain embodiments, the kits according to the invention comprise: (a) an intravaginal light-based treatment device (ILTD) (100) according to any of the embodiments above; and (b) two or more coatings (104) designed to be used by said ILTD. In such kits, the ILTD can be re-usable and before each use the user only needs to replace the coating (104). Optionally, after all coatings in the kit are used, the ILTD is also discarded, or the user may purchase new coatings.

In certain embodiments, the kits according to the invention comprise: (a) an intravaginal light-based treatment device (ILTD) (100) according to any of the embodiments above; and (b) two or more main bodies (101), optionally with coatings (104) designed to be used by said ILTD. In such kits, the ILTD comprises an external casing (107) with a power source (103) and a light source (102) that is designed to be re-usable and before each use the user replaces the main body (101) and/or its coating (104). Optionally, after all main bodies (101) (and coatings) in the kit are used, the ILTD (i.e., the external casing (107)) is also discarded.

In certain embodiments of the kits according to any of the embodiments above, the coatings (104) in each kit are the same or different. For instance, a single kit may comprise 5 coatings, each having different properties, such as active agent content, moisture materials, hormones, photosensitizers, therapeutics, buffer material(s) and/or biome, e.g., for providing different treatment in each day throughout the treatment of the disorder. For instance, in the first and second days the coating is designed to release buffer material to bring the pH to a desired pH; in the second and third days, the coating is designed to release a therapeutic compound; and in the third and fourth days the coating is designed to release a different therapeutic compound and optionally additional buffering material. Alternatively, some or all of the coatings in the kit may be the same.

In certain embodiments, of the kits according to any of the embodiments above, the light source (102) of each ILTD in the kit is different from that of another ILTD in the kit. For instance, the kit may comprise 5 different ILTDs or 5 different main bodies (101) (and a single external casing (107) with the power source), each ILTD or main body (101) having a different light source, e.g., in terms of wavelength, intensity and/or pattern (pulsed/continuous), for providing different light treatment in each day throughout the treatment of the disorder. For instance, in the first and second days the light source is designed to emit red-light, optionally in different intensities or pattern; in the second and third days, the light source is designed to emit blue-light, optionally in different intensities or pattern; and in the third and fourth days the light source is designed to emit both red- and blue-light at a different intensity and/or pattern from that of previous days.

In certain embodiments, the kits according to any of the embodiments above further comprise a conduit designed to assist in the insertion of the ILTD into the vagina and/or an instructions pamphlet.

In certain embodiments, the kits of the invention comprise various ILTDs in any size and shape. For instance, a kit can comprise multiple sized ILTD, e.g., small (e.g., 2.5 cm in length); medium (5 cm in length); and large (7 cm in length), and/or with different diameter (e.g., from about 0.8 cm to about 1.5 cm, such as 1 cm), to enable a user to try and decide which size fits best.

As noted, the ILTD according to the invention is designed for use in methods of treating various disorders and conditions in the vagina of a female patient. Accordingly, in another aspect, the present invention provides methods of treatment or prophylaxis of various conditions and disorders, including opportunistic infections, in a patient by inserting into the patient's vagina the ILTD according to any of the embodiments above and activating same. The present invention further provides the ILTD according to any of the embodiments above for the treatment or prophylaxis of various conditions and disorders, including opportunistic infections, in a subject in need thereof.

In certain embodiments, the present invention provides methods of treatment or prophylaxis, the methods includes: (a) identifying a female subject likely to have been, or likely to be, exposed to an infectious microorganism, such as fungal, viral or bacterial; and (b) administering/inserting into the subject's vagina the ILTD according to any of the embodiments above designed to kill or inhibit the growth of the infectious microorganism. In specific embodiments, the ILTD further controls the pH of the vagina's environment using a buffer compound, and/or releases one or more active agents designed to kill or attenuate the growth of such infectious microorganism.

In certain embodiments, the present invention provides a light-based method of treatment or prophylaxis of a vaginal disorder, including opportunistic infections, in a patient, the method comprising: (1) providing an intravaginal light-based treatment device (ILTD) (100) for treating patient's vaginal disorders, the ILTD comprises: (a) a main body (101); (b) a light source (102); (c) a power source (103); (d) optionally, a coating (104) over said main body (101); and (c) a tether (105), wherein said light source is designed to emit pulsed light having at least one predefined wavelength suitable for treating said vaginal disorders, and said main body (101) and coating (104) are designed to allow said light to pass through and reach vaginal tissue; said light source is designed to emit said light at predefined intervals and intensities suitable for treating said vaginal disorders; and said tether (105) is connected to said main body (101) and is designed to be used for retracting the ILTD outside from the patient's vagina; (2) inserting the ILTD into the vagina of the woman; and (3) activating the ILTD thereby illuminating the vagina interior.

In certain embodiments, the present invention provides a light-based method of treatment or prophylaxis of a vaginal disorder, including opportunistic infections, in a patient, the method comprising: (1) providing an intravaginal light-based treatment device (ILTD) (100) for treating patient's vaginal disorders, the ILTD comprises: (a) a main body (101); (b) a light source (102); (c) a power source (103); (d) optionally, a coating (104) over said main body (101); (c) a tether (105); and (f) one or more active agents selected from: moisture materials, hormones, photosensitizers, therapeutics, buffer material, and/or biome, or any combination thereof, wherein said light source is designed to emit either a continuous/constant light or a pulsed light at predefined intervals and intensities suitable for treating said vaginal disorders, having at least one predefined wavelength suitable for treating said vaginal disorders, and said main body (101) and coating (104) are designed to allow said light to pass through and reach vaginal tissue; said device or coating is designed to release said one or more active agents into the vagina; and said tether (105) is connected to said main body (101) and is designed to be used for retracting the ILTD outside from the patient's vagina; (2) inserting the ILTD into the vagina of the woman; and (3) activating the ILTD thereby illuminating the vagina interior.

Opportunistic infections can be a result of use of antibiotics (both prophylactic and therapeutic) as well as immunosuppressive and cytotoxic drugs; indwelling foreign bodies, including prosthetic heart valves, prosthetic joints, and intravascular monitoring devices; venous, arterial, urinary, and peritoneal catheters; and organ, cell, or tissue transplantation. Subjects with a compromised immune system are also predisposed to infection (e.g., fungal infection) and stand to benefit from this invention. Such subjects can have one or more of the following conditions: deficiency of neutrophils (neutropenic), deficiency of T-cells (lymphopenic), mucous membrane toxicity, or any one or several of a group of immune disorders (e.g., chronic granulomatous disease, Job's syndrome, AIDS, and other T-cell deficiencies). Subjects can also have one or more of a variety of cancers, including, without limitation, lymphoma, leukemia, or breast cancer. Such subjects may have undergone or are undergoing cancer treatment (e.g., radiotherapy, chemotherapy, gene therapy, immunotherapy, angiogenesis therapy, donor cell transplantation or infusion, or stem cell therapy).

In addition, certain active agents that may be released from the ILTD may also have an effect on the cells' permeability. In certain embodiments of the methods of the invention, the ILTD is designed to change the permeability of the vaginal mucus and/or of the pathogen's membrane to thereby facilitate treatment. Such permeability modification can be obtained by any number of ways, such as, by using specific irradiation parameters as detailed above, which result with increased stress onto specific pathogens, and/or due to the release of active agent(s) that influence the cells' membrane permeability from the ILTD. In such cases, permeability modification is affected by the medication, and the light produces stress in the pathogen cell. The use of both light and active agent(s) release to influence the cells' membrane permeability, creates a synergistic combined effect that lowers the viability of the pathogen cell. In certain embodiments, permeability increase is obtained by release of DMSO from the ILTD.

In certain embodiments, the above method further comprises one or both of the following steps: (i) releasing an effective amount of an active agent, such as moisture materials, hormones, photosensitizers, therapeutics, buffer material(s) and/or biome from said ILTD into the vagina; and (ii) replacing one ILTD with another daily.

In certain embodiments, the above methods demonstrate a synergistic effect on the treatment and prophylaxis of the vaginal disorder to be treated.

As used herein, the term "prophylaxis" means complete prevention of the symptoms of a disease, a delay in onset of the symptoms of a disease, or a lessening in the severity of subsequently developed disease symptoms. As used herein, "therapy" can mean a complete abolishment of the symptoms of a disease or a decrease in the severity of the symptoms of the disease.

In certain embodiments, the above methods further comprise a step of orally or topically administering to the patient a therapeutically effective amount of one or more active agents, designed to work with the ILTD to obtain a synergistic effect. Such separate administration can be either before, after or during the treatment with the ILTD.

The subject can have an infection, or be predisposed to an infection, with any of the infectious microorganisms listed in this document. The compounds can be administered either before, simultaneous with, or after the administration of one or more supplementary agents. Supplementary agents can include, for example, anti-fungal agents, modulators of immune function, or antibiotics.

In certain embodiments of the above methods, activating of the ILTD is carried out by any one of: (i) pressing or turning an activation switch; (ii) removing a protective cover from the ILTD or said coating (104); (iii) removing an electric barrier from the power source (103) thereby enabling passage of power therefrom to the light source (102); or (iv) breaking or removing a barrier within the ILTD thereby mixing two or more reagents together, which results with generation of light.

In specific embodiments of the above methods, all the ILTDs have the same activity. In alternative specific embodiments, each ILTD used has a different activity compared to the previously used ILTD. The term "different activity" as used herein means: (i) releasing a different active agent or agents; (ii) illuminating light at a different wavelength and/or intensity; (iii) illuminating light at a different manner, e.g., continuously or pulsed, or in different puled manner; or any combination thereof.

In specific embodiments, the infectious microorganism is of a genus selected from the group consisting of *Candida, Eayst, Gardnerella, Haemophilus, Bacteroides, Bordetella, Fusobacterium, Prevotella, Porphyromonas*, Atopobium, Mobiluncus, *Peptostreptococcus, Mycoplasma*, and *Ureaplasma*.

In certain embodiments of the above methods, the infectious fungal microorganism can be any of a variety of yeasts, e.g., *Candida* species fungi (e.g., *Candida albicans, Candida tropicalis, Candida parapsilosis, Candida glabrata, Candida krusei, Candida pseudotropicalis, Candida lusitaniae*, or *Candida guilliermondi*), *Cryptococcus* species fungi (e.g., *Cryptococcus neoformans*), or the yeast phases of dimorphic fungi. Dimorphic fungi include, e.g., the above *Candida* species, *Histoplasma capsulatum, Blastomyces dermatitidis, Paracoccidioides brasiliensis, Coccidioides immitis*, or *Sporothrix schenckii*. The method can be applied to the hyphal phase as well as the yeast phases of these dimorphic fungi. Infectious fungal microorganisms can also be monomorphic fungi, for example, dermatophytes (ringworms), *Pneumocystis carinii*, Zygomycetes, *Malassezia furfur, Fusarium* species *fungi, Cladosporium* species *fungi, Pseudoallescheria boydii, Penicillium* species *fungi* (e.g., *Penicillium marneffei, Penicillium chrysogenum*, or *Penicillium citrinum*), or *Aspergillus* species fungi (e.g., *Aspergillus fumigatus, Aspergillus flavus*, or *Aspergillus niger*).

Non-limiting examples of bacteria of interest are: *Gardnerella vaginalis, Haemophilus influenzae, Haemophilus ducreyi, Haemophilus aegyptius* (a variety of *Haemophilus influenzae*), *Haemophilus parainfluenzae, Haemophilus hemolyticus, Haemophilus suis, Bordetella pertussis* (related to *Haemophilus*), *Bordetella parapertussis, Bordetella bronchoseptica, Bacteroides* bacteria (e.g., *B. fragilis, B. thetaiotaomicron, B. vulgatus, B. ovatus, B. distasonis, B. uniformis, B. stercoris, B. eggerthii, B. merdae, and B. caccae*), *Prevotella melaninogenica* (previously designated *Bacteroides melaninogenicus*) and other *Prevotella* species (e.g., *P. bivia, P. buccae, P. corporis, P. dentalis, P. denticola, P. disiens, P. enocca, P. heparinolytica, P. intermedia, P. loeschii, P. nigrescens, P. oralis, P. oris, P. oulora, P. tannerac, P. venoralis, and P. zoogleoformans*), *Fusobacterium* bacteria (e.g., *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum* polymorphum, *F. nucleatum vincentii, F. periodonticum, F. russii, F. ulcerans, and F. varium*), *Porphyromonas* bacteria (e.g., *P. asaccharolytica, P. cangingivalis, P. canoris, P. cansulci, P. catoniae, P. circumdentaria, P. crevioricanis, P. endodontalis, P. gingivalis, P. gingivicanis, P. gulae, P. levii, P. macacae, P. salivosa*), *Atopobium* bacteria (e.g., *A. fossor, A. minutum, A. parvulum, A. rimae, and A. vaginae*), *Mobiluncus* bacteria (e.g., *M. curtisii* (including subspecies *curtisii* and *holmesii*), and *M. mulieris*), *Peptostreptococcus* bacteria (e.g., *P. anaerobius, P. asaccharolyticus, P. harei, P. hydrogenalis, P. indoliticus, P. ivorii, P. lacrimalis, P. lactolyticus, P. magnus, P. micros, P. octavius, P. prevotii, P. trisimilis, P. tetradius, and P. vaginalis*), *Mycoplasma* bacteria (e.g., *M. pneumonia, M. buccale, M. faucium, M. fermentans, M. salivarium, M. arthriditis, M. hominis, M. orale, M. genitalium, M. penetrans, M. lipophilum, M. laidlawii, M. pirum, M. pulmonis, M. mycoides, M. gallisepticum, M. hyopneumoniae, and M. mobile*), and *Ureaplasma* bacteria (e.g., *U. urealyticum* and *U. parvum*).

In another aspect, the present invention provides methods of diagnosing or monitoring of various conditions and disorders in a patient's vagina by inserting into the vagina the ILTD according to any of the embodiments above and activating same. In specific embodiments, the method comprises the steps of: (a) providing an intravaginal light-based treatment device (ILTD) (100) of the invention comprising: (i) a main body (101); (ii) a light source (102); (iii) a power source (103); (iv) optionally, a coating (104) over said main body (101); (v) a tether (105); optionally (vi) one or more active agents selected from: moisture materials, hormones, photosensitizers, therapeutics, buffer material, and/or biome, or any combination thereof; and any one of: (1) a camera designed to capture images of the vagina's inner walls; (2) pH-sensor or pH-meter (109) designed to measure the pH inside the vagina; and (3) a thermometer or temperature-sensor designed to measure the temperature inside the vagina; (4) moisture sensor; and (5) a data-transmitter designed to transmit data from said camera, pH-meter (109) and thermometer to a remote computing system; (b) inserting said ILTD into the vagina of said woman; (c) activating said ILTD thereby gathering data from within the vagina and transmitting same to a remote computing system; and (d) analyzing said data and diagnosing said vaginal disorder or monitoring its condition.

In certain embodiments, the above diagnosing or monitoring method further comprises step of replacing one ILTD with another daily and/or a step of treating said vaginal disorder based on the diagnosis or condition thereof. Such treatment can be by light therapy and/or by releasing an effective amount of an active agent, such as moisture materials, hormones, photosensitizers, therapeutics, buffer material(s) and/or biome from said ILTD into the vagina, as detailed hereinabove.

In certain embodiments of the above diagnosing or monitoring methods, the activation said ILTD is carried out by: (i) pressing or turning an activation switch; (ii) removing a protective cover from the ILTD or said coating (104); or (iii) removing an electric barrier from the power source (103) thereby enabling passage of power therefrom to the light source (102).

Notably, the patient can be any mammalian subject, including humans, non-human primates, horses, cattle, pigs, sheep, goats, dogs, cats, rabbits, guinea pigs, etc.

It should be noted that although the application relates explicitly to a female vagina, it is to be understood that the ILTD and methods according to invention can be used in any other cavity or intracavity, such as rectum, intestine, peritoneal, uterus, UTI, pleural, and pericardial, or in/on other tissues, such as skin, mucosal tissue, and sinuses.

The present invention provides many benefits and advantages over known methods and devices, such as: providing an easy and simple way to administer active agents to the site of infection/disorder; provide phototherapy in conjunction with administration of active agents; remote diagnostic of vaginal (or any other inner cavity) conditions; monitoring and controlling the pH and other parameters in the vagina, including the biome; and sink heat from the vagina during light therapy.

Unless otherwise indicated, all numbers referring, e.g., to amounts of lanthanum oxycarbonate, lanthanum oxide, or lanthanum oxychloride, nickel, and nickel oxide in the supported catalyst disclosed herein, or to temperatures used in the process of the invention, used in the present specification are to be understood as being modified in all instances by the term "about". Accordingly, unless indicated to the contrary, the numerical parameters set forth in this description and claims are approximations that may vary by up to plus or minus 10% depending upon the desired properties sought to be obtained by the invention.

Several embodiments of the invention have been described. Nevertheless, it will be understood that various modifications may be made without departing from the spirit and scope of the invention. Accordingly, other embodiments are within the scope of the following claims.

The invention will now be illustrated by reference to the accompanying drawings which are to be considered only as representative examples of possible embodiments of packages of the invention.

FIGS. 1A-1D are schematic illustrations of an intravaginal light-based treatment device (ILTD) according to the invention. As seen in FIG. 1A, the assembled ILTD (100) has a tampon-like shape that can be easily inserted into the vagina, and a tether (105) is present to enable its extraction at the end of use. As seen in FIGS. 1B and 1C, the tether (105) is part of a cap that can be screwed onto the main body (101), e.g., to enable assembly of the ILTD during manufacture—as illustrated the power source (103) and the light source (102) are inserted into a coating (104) that together with the cap generate the complete main body (101). Alternatively, the ILTD is manufactured as a single unit without the ability to open and reach the inside of the main body (101). FIG. 1D is another possible configuration of the ILTD (100) shown in FIGS. 1A-1C, this time with a pH-meter (109) near the light source. The pH-meter (109) is connected-to and receives power from the power source (103). Also seen is that the coating (104) is transparent.

Figures 2A, 2B:
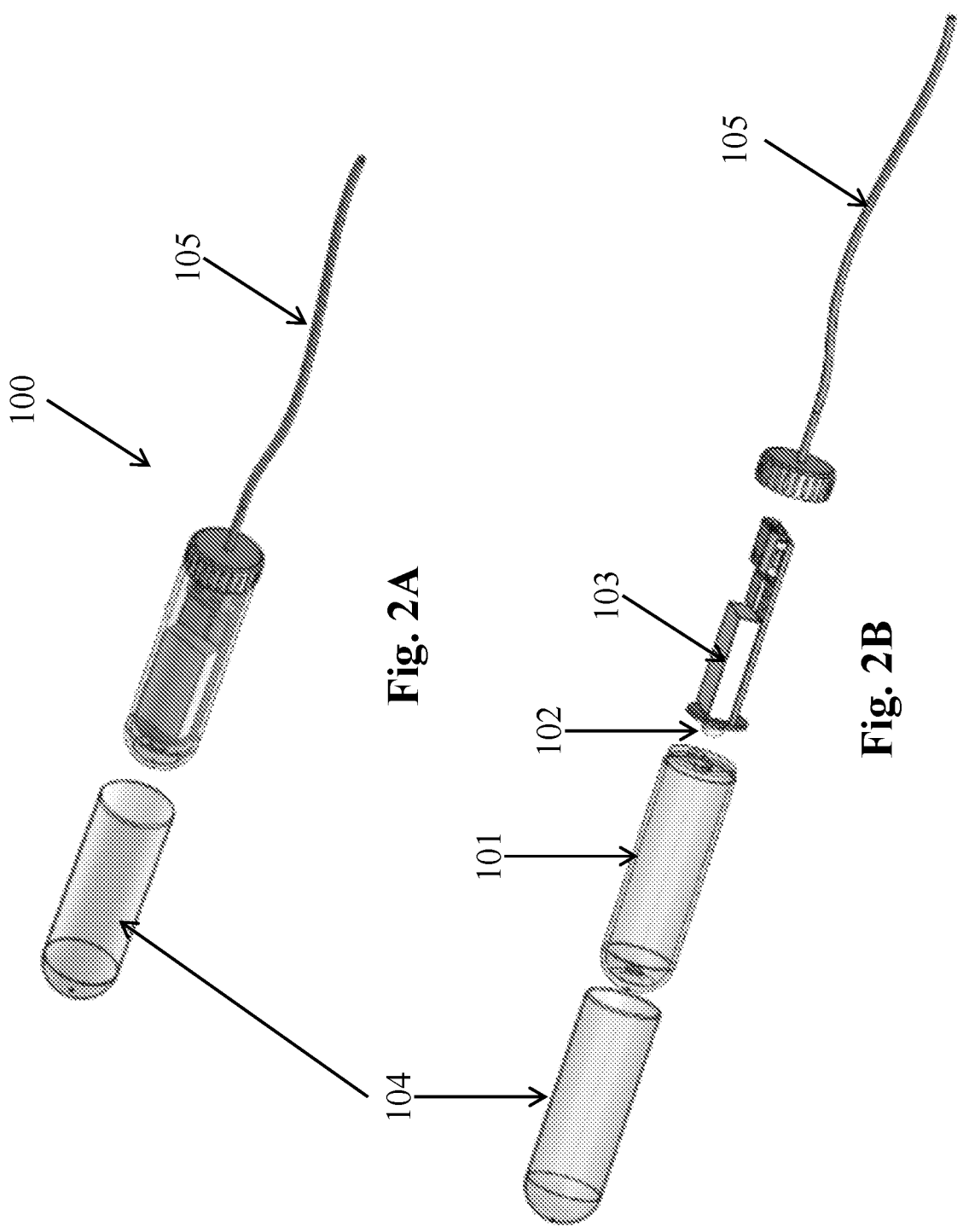
FIGS. 2A-2B are schematic illustrations of another ILTD according to the invention with a rechargeable battery.

FIGS. 2A-2B demonstrate another configuration of an ILTD of the invention, this time with an integrated rechargeable battery as the power source (103). Also illustrated is a configuration in which the main body (101) is a unified single unit that comprises both the power source (103) and the light source (102), and constitutes an independent unit, that is optionally assembled during manufacture as illustrated in FIG. 2B or fabricated in such a way that does not enable the user to dismantle it. In both cases, it is illustrated that a coating (104) can be mounted onto the main body (101). Also seen is that both the main body (10) and the coating (104) are transparent to allow light from the light source (101) to pass therethrough.

As illustrated in FIGS. 1 and 2, the main body (101) constitutes essentially entirely from the power source (103) and the light source (102).

In addition, the tether (105) can be used as a heat conduit to remove excess heat generated, e.g., by the light source (102), from the ILTD (100) and away from the vagina, in order to prevent overheating of the tissue.

Figures 3A, 3B:
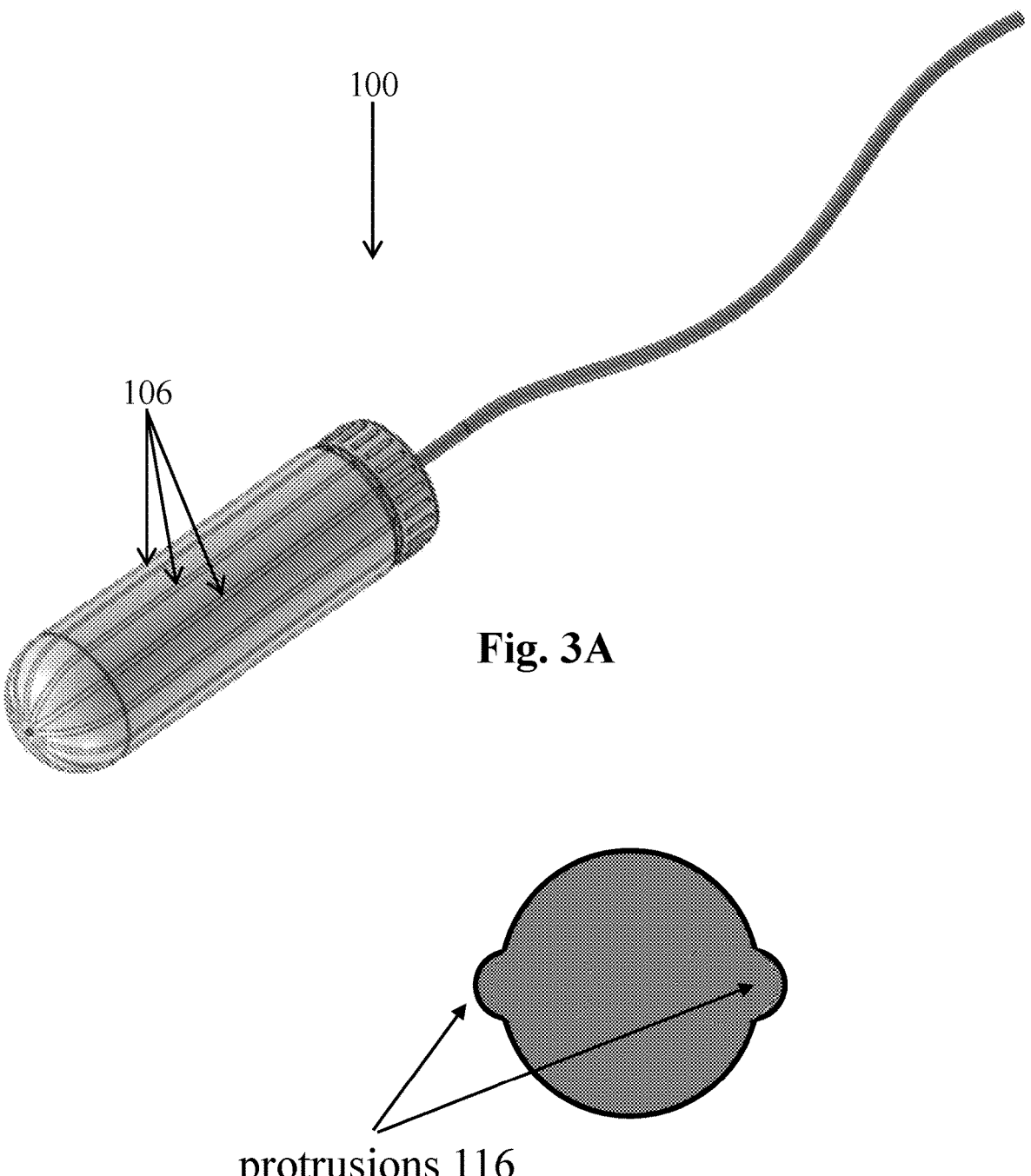
FIG. 3A is a schematic illustration of an ILTD with a grooved coating.
FIG. 3B is a cross-section of a Direction-maintaining Device designed to maintain the ILTD of the invention in a desired position.

FIG. 3A provide an external view of an ILTD, illustrating the possibility of preparing the main body (101) or the coating (104) in a grooved manner. Such regions (106) may act as anti-slip regions designed to assist the ILTD (100) to remain in place after insertion into the vagina. In addition, such regions (106) may increase the overall surface area of the coating (104), which increases contact area with the vagina's walls thereby facilitating enhanced release rate of therapeutic agent(s) from the ILTD/coating to the tissue, thus improving treatment efficiency.

FIG. 3B provide a cross-sectional view of an ILTD, illustrating the possibility of preparing the main body (101) or the coating (104) in such a way that it includes protrusions (116). Such protrusions (116) may act as anti-slip regions designed to assist the ILTD (100) to remain in place after insertion into the vagina. In addition, such protrusions (116) may increase the overall surface area of the coating (104), which increases contact area with the vagina's walls thereby facilitating enhanced release rate of therapeutic agent(s) from the ILTD/coating to the tissue, thus improving treatment efficiency. In addition, such protrusions (116) may assist in accurate placement of the ILTD within the vagina in order to emit light in a desired direction/orientation.

Figure 4:
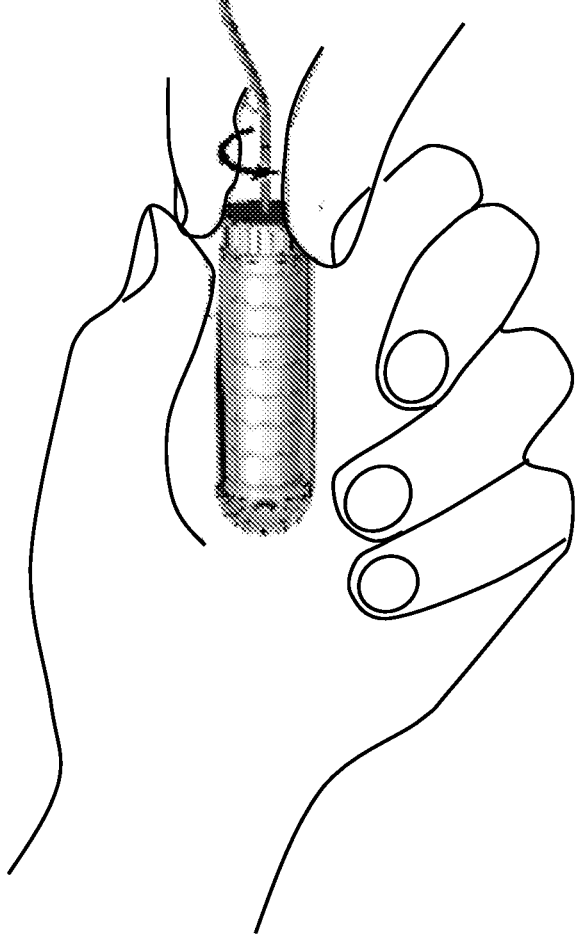
FIG. 4 is a schematic illustration showing activation of an ILTD by turning a switch at the ILTD's bottom section.

As explained above, the ILTD (100) can be activated, i.e., turning the light on, prior to the insertion of the ILTD into the vagina. FIG. 4 illustrates such activation by a simple turning of the bottom section of the main body (101) immediately before insertion of the ILTD into the vagina. Notably, many other activation techniques are possible, such as wirelessly activation via an App., or via a switch located on an external casing (107).

Figures 5A, 5B:
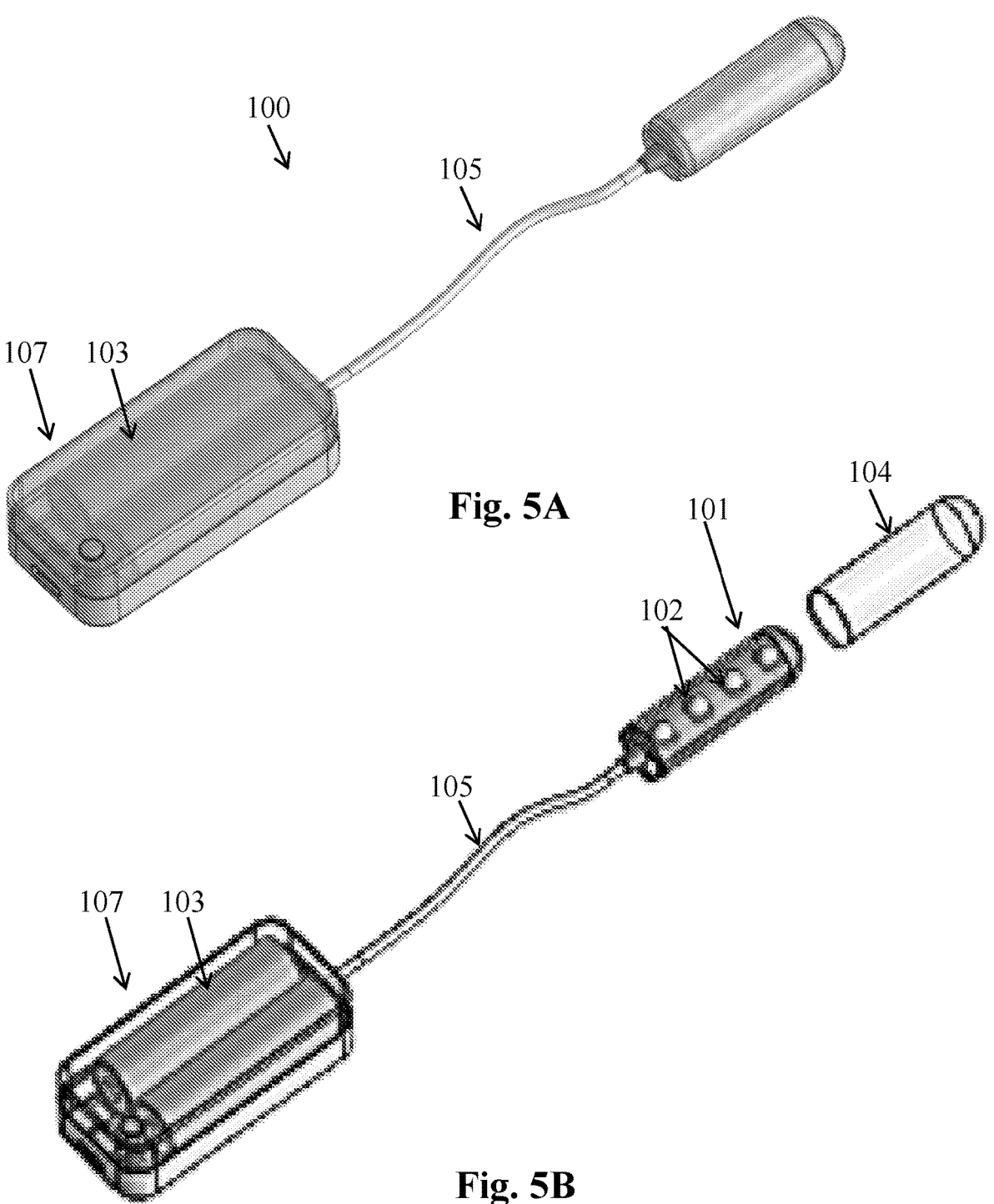
FIGS. 5A-5B are schematic illustrations of another ILTD according to the invention with an external power source and an internal light source.

FIGS. 5A-5B provide yet another alternative of an ILTD (100) of the invention, in which the power source (103) is located in an external casing (107) connected to the main body (101) via the tether (105). As illustrated, in this example the main body (101) is transparent and contains the light source (102). In this example, the light source (102) constitutes of multiple LEDs distributed along the main body (101) on both sides (not shown).

Figures 6A, 6B:
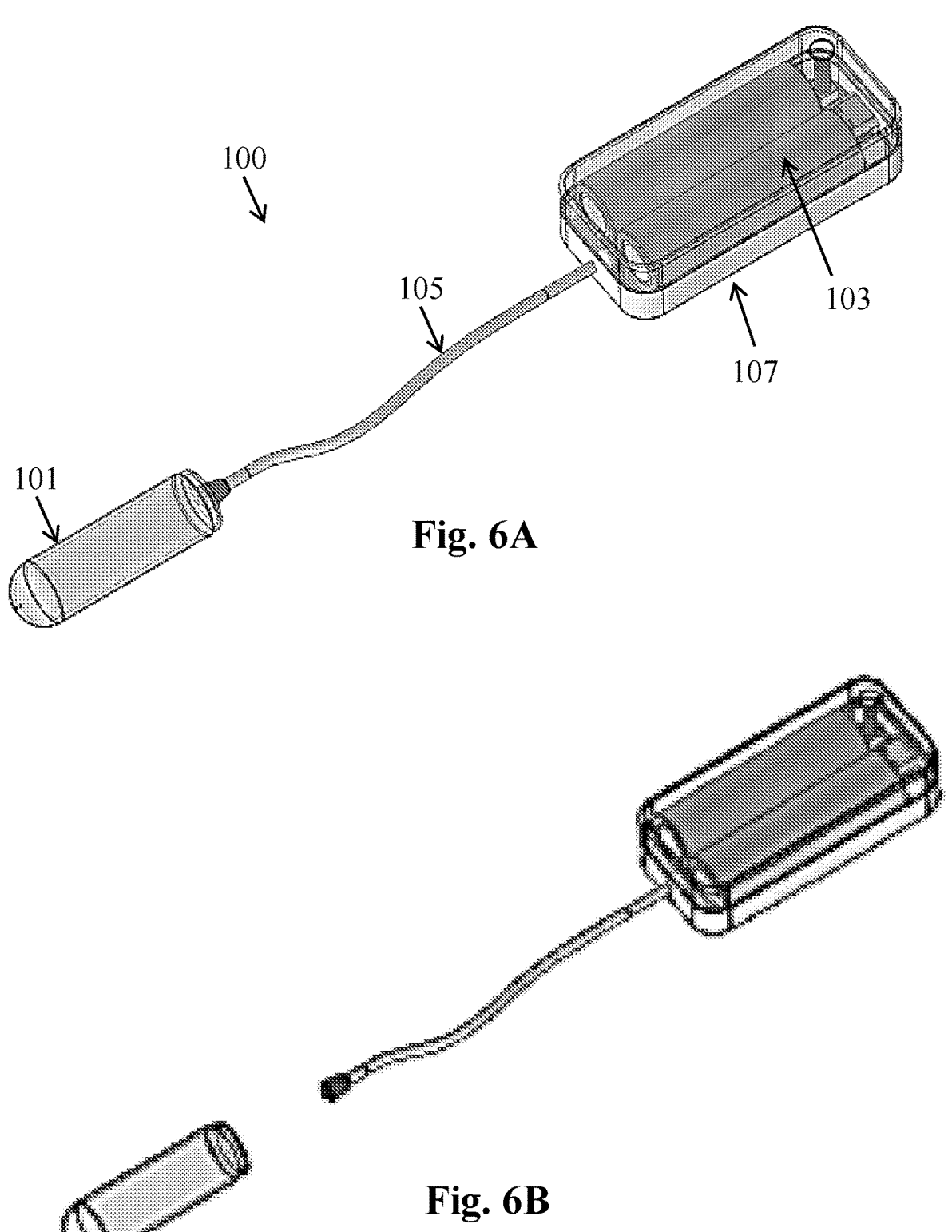
FIGS. 6A-6B are schematic illustrations of another ILTD according to the invention with external power source and light source.

FIGS. 6A-6B provide yet another alternative of an ILTD (100) of the invention, in which the power source (103) and the light source are both located in an external casing (107) connected to an empty transparent hollow main body (101) via a tether (105) that acts also as an optic-fiber. It is noted that in such a configuration, any heat that might be generated by the light source or the power source is actually generated outside the vagina, i.e., in the external casing (107), and thus the tether (105) does not need to act as a heat conduit. As illustrated in FIG. 6B, the transparent hollow main body (101) may be detachable from the tether (105), thereby enabling replacing same before each use.

Figures 7A, 7B, 7C:
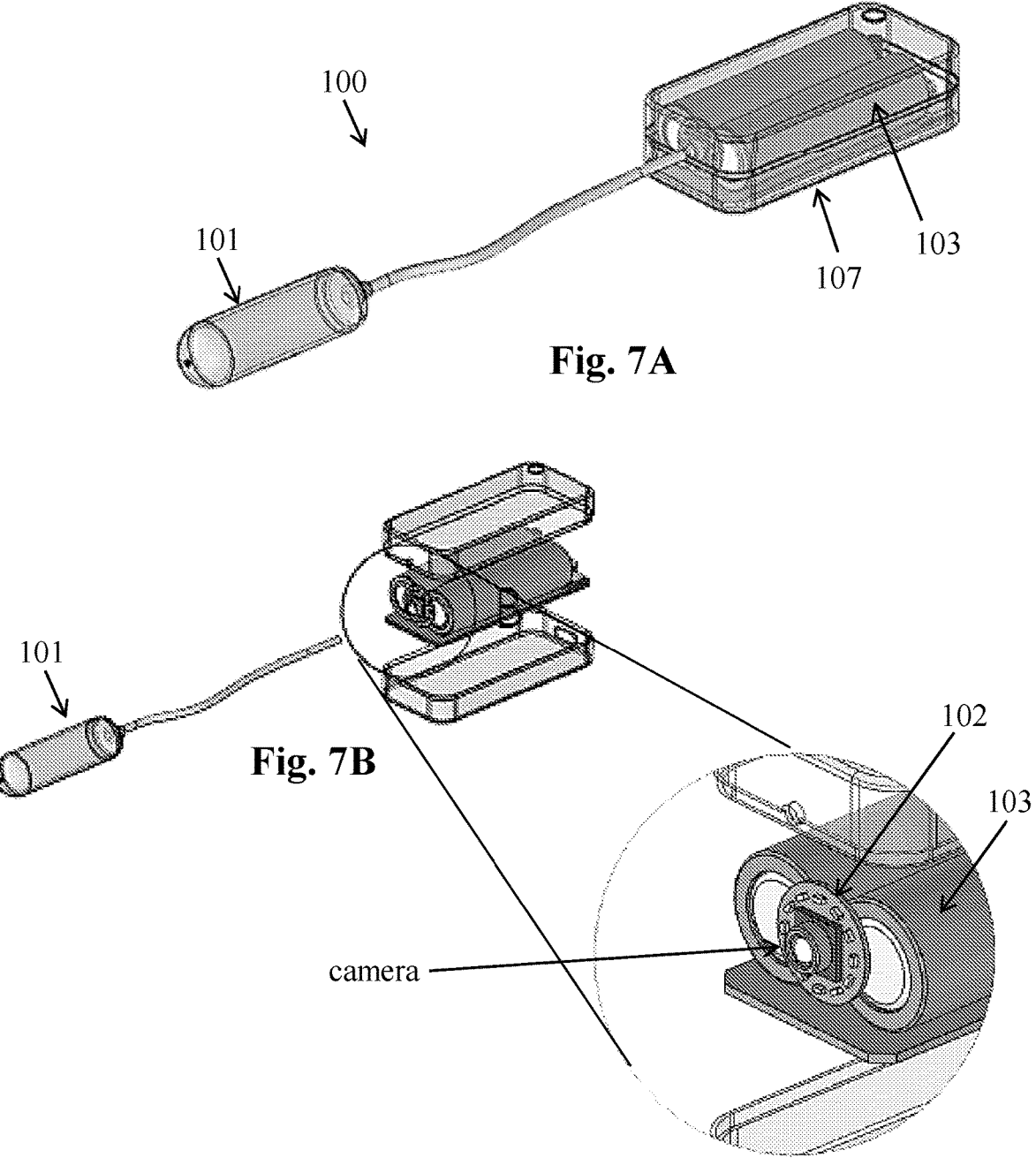
FIGS. 7A-7C are schematic illustrations of another ILTD according to the invention with an external power source, light source, and camera.

FIGS. 7A-7C are similar illustration of the ILTD of FIG. 6, now with a camera unit near the light source (102). In such a configuration, the ILTD (101) can take images of the inner wall of the vagina using the illumination generated by the light source, and the tether (105) also acts as means to enable the camera to take pictures (or movies).

It should be noted that the external casing (107) and the power source (103) may be re-usable, e.g., by using rechargeable batteries, or by enabling replacing the batteries if needed. In such cases, the transparent hollow main body (101) is either disposable, i.e., can be detached from the tether (105) after each use, or may also be re-usable, in which case, only the coating (104) is removed therefrom before each use.

Notably, when referring hereinabove to the detaching of the main body (101) from the tether (105), an alternative configuration is that the tether (105) is associated with the main body (101), and the replacement thereof is carried out be detaching the tether (105) from the external casing (107).

Figure 8A:
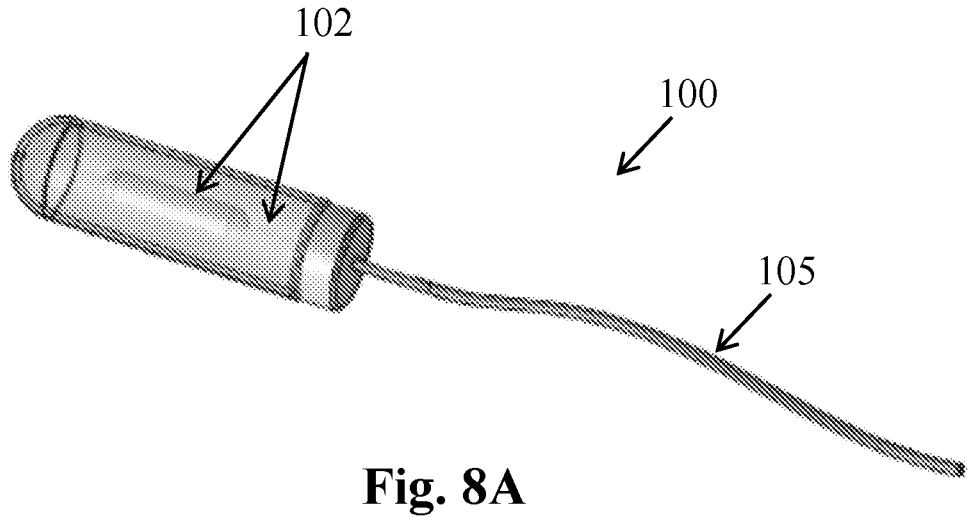
FIGS. 8A-8B are schematic illustrations of another ILTD according to the invention with a chemical light source.
Figure 8B:
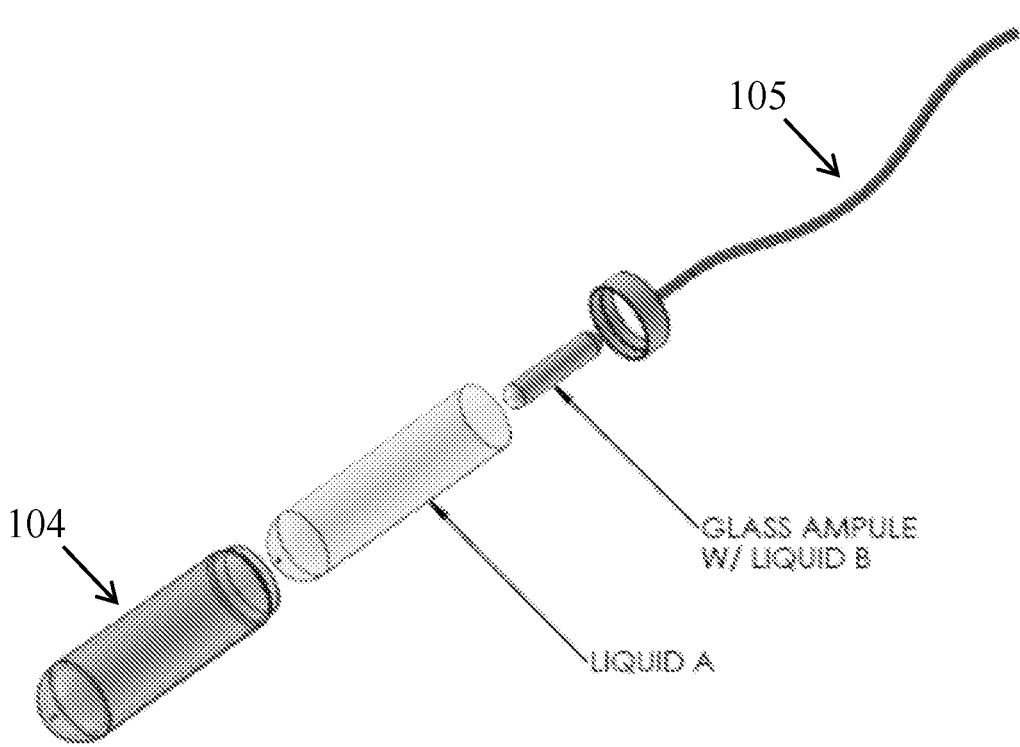

FIGS. 8A-8B are schematic illustrations of an alternative ILTD of the invention, equipped with a chemical light source: as illustrated, the main body holds one chemical and a vial with another chemical. The breaking of the inner (glass) vial leads to the release of its content and the mixing of the two chemicals, thereby creating a chemical reaction that cause illumination of light. As explained above, the breaking of the inner vial may be carried out immediately prior to insertion of the ILTD into the vagina, or after, e.g., using an electronic means. An alternative configuration of such a chemical-based ILTD, is a main body (101) with two compartments, each holding a different chemical, and the breakage or removal of the barrier between the compartments, leas to the mixing of the chemicals and illumination. Notably, if the chemical reaction involves heat generation in addition to light illumination, the tether (105) act also here as a heat conduit to remove excess heat away from the vagina to prevent its overheating.

Figure 9:
FIG. 9 is a schematic illustration showing a wirelessly data transmission from an ILTD to a smartphone.

FIG. 9 provides an illustration of how data is transmitted wirelessly from the ILTD (100) to a smartphone. Such data can be instructions delivered from the smartphone to the ILTD (100), e.g., to activate or deactivate the light source, to release an active agent, to take pictures, etc., and/or data delivered from the ILTD (100) to the smartphone, e.g., data regarding pH, temperature, pictures/movies taken, etc.

FIG. 10A is a diagram illustrating one possible mode of activation of the ILTD according to certain embodiments of the invention, in which the ILTD does not include active agents, and is designed to treat the vaginal disorder using light pulses with specific pulse width and duty cycle. As illustrated, after the ILTD is inserted into the patient's vagina and activated, it emits light according to a predefined protocol or according to a duty cycle determined by a computing system based on measurements received by the different sensors within the ILTD.

FIG. 10B is another diagram illustrating another possible mode of activation of the ILTD according to certain embodiments of the invention, in which the ILTD does include active agents, and is designed to treat the vaginal disorder using both specific irradiation parameters and release of the active agents (either from the main body or from the coating). As illustrated, after the ILTD is inserted into the patient's vagina and activated, it emits light and releases one or more active agents according to a predefined protocol or according to a irradiation regimen determined by a computing system based on measurements received by the different sensors within the ILTD.

Figure 11A:
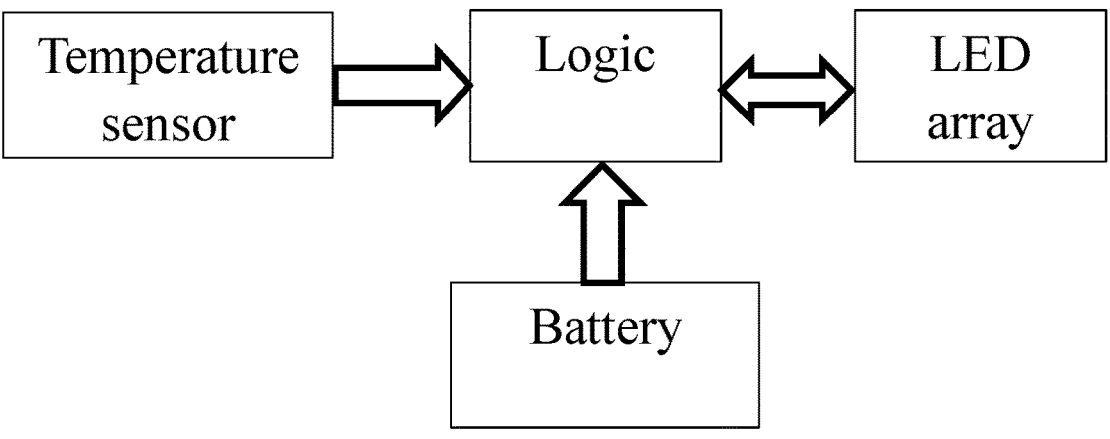
FIGS. 11A-11B are diagrams illustrating possible components of the ILTD of the invention.
Figure 11B:
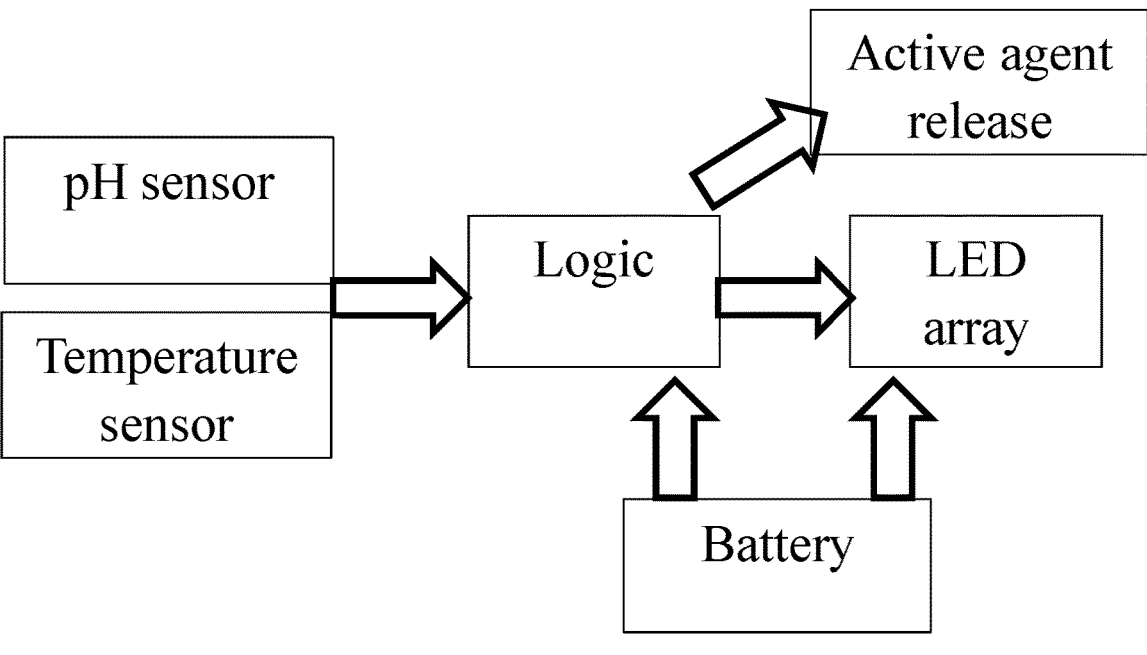

FIGS. 11A-11B illustrate possible components of the ILTD of the invention and the relationship therebetween: for instance, the computing system ("logic") may receive data from various sensors, such as a pH-sensor and a temperature sensor, analyze the received data and determine an operation protocol for the light source, and/or for the release of the active agent(s).

EXAMPLES

Example 1: Proof-of-Concept (POC) Study

The in vitro is designed to verify the capability of blue light irradiation (at a wavelength of 405 nm) to significantly reduce a fungal population, typically of candidiasis.

It is known in the literature that fungal concentration in the order of 106/ml are considered as an indication of excessive infection, while fungal concentration in the order of 102-103 ml are considered asymptomatic. Thus, a treatment that reduces the concentration in the order of 3 to 4 $Log_{10}$ is considered to be a basis for an effective therapy.

The killing effect of blue light irradiation of blue ILTD was tested at HYLabs.

Device and Setup: A dedicated 405 nm device was used to irradiate *C. albicans* colonies that were seeded in 5 wells of a 24-well microplate. Additional wells that were out of the irradiated area served as control: 4 wells were filled with similar *C. albicans* concentrations—as positive control, and 2 wells filled with saline—as negative control.

The 24-well microplate was placed in a constant temperature bath that was set to 36° C. The temperature of the irradiated wells was monitored to be in the range of 36° C. to 39° C. The bath was completely covered with aluminum foil to block stray, external light.

Results and Discussion: Following a 3-hour irradiation period, the samples were harvested, and the amount of *C. albicans* remaining post irradiation was assessed. No *C. albicans* were found in any of the wells: the study has proven complete eradication of *C. albicans*—a reduction of at least 6 orders of magnitude (6 $log_{10}$) in all wells.

Several follow-up tests validated that no external or internal factors contributed to these results.

Example 2: Study Report

Microbiology Background

Vulvovaginal candidiasis (VVC) is a mucosal infection in the vaginal tissue and the vulva in the female reproductive tract. VVC is predominantly (>90%) caused by *Candida albicans*, an opportunistic fungal pathogen. The remaining 10% are caused by the non-*albicans Candida* (NAC) species, such as *C. glahrata, C. krusei, C. tropicalis* and *C. parapsilosis*. VC is reported as the second most common cause of vaginitis, and it is estimated that 75% of all women will suffer from VVC in their childbearing years, with up to 140 million of these women developing recurrent VVC (RVVC), within 1 year. Despite the extremely high prevalence of VVC worldwide, treatment options for RVVC remain limited, with many failures with frontline azoles treatment. Furthermore, the causes of onset and recurrence of the disease are largely unclear, with just a few studies identifying potential mechanisms of treatment failure. *C.*

*albicans* concentrations in the order of 102-103 ml are considered asymptomatic for non-pregnant women. Concentrations that range between 104-106 are indicative of excessive infection. Hence, a treatment that can decrease the *C. albicans* concentration by 3 to 4 $Log_{10}$ may be considered as a basis for effective therapy.

The cell line that was used by HyLabs in this experiment was *Candida albicans* ATCC 10231. The colony of this *C. albicans* cell-line in a saline solution is stable, and without nutrients (such as glucose, or any other sugar) in the medium, the colony cannot proliferate—just survive. Thus, any change in the *C. albicans* concentration in the experiment is solely due to the irradiation, and not affected by the variance of proliferation of the fungus in the wells.

The Irradiation Device for the Study

An irradiation device was designed to fit a microplate with 14 high power, 405 nm LEDs, connected on a PCB, to an 80 mm long line, powered by 60 to 500 mA/LED current. These LEDs include a lens to limit their light emission angle to 120° (typical). The device was designed to be placed at 18 mm over the microplate. Thus, the 2.2 mm lens on the LED should emit light to ~30 mm on each side of the microplate, below the LED line.

In order to limit the temperature increase to the irradiated area to below 4° C. above body temperature, the LED PCB was mounted on an aluminum bracket that served as a heatsink (using a temperature conducting acrylic adhesive). To remove most of the irradiated heat, a 25 mm fan was installed to vent the air between the LED line and the microplate. Two units of bracket-mounted LED lines, plus 2 fans were assembled on a glass-epoxy panel to ensure mechanical stiffness and repeatability versus the 24-well microplate.

TABLE 1

| The operating parameters of the LEDs in the ILTD | | |
|---|---|---|
| Operation parameters | Values | Units |
| LED current (per LED) | 350 | Ma |
| Power (per LED) | 1.2 | W |
| Number of LEDs in an array | 14 | U |
| Total power per array | 16 | W |

TABLE 2

| Main photoelectric parameters per LED | | | | | |
|---|---|---|---|---|---|
| | Symbol | Test conditions | Typical value | Min. value | Max. value | Unit |
| Forward voltage | VF | IF = 700 ma | — | 3.2 | 4 | V |
| Forward current | IF | — | — | — | 700 | Ma |
| Optical current | IV | — | — | — | 1300 | mW |
| Beam angle | 2 ol/2 | IF = 700 ma | 60 | 120 | — | * |
| Wavelength | λ | IF = 700 ma | 400 | 405 | 410 | Nm |
| Thermal resistance | R | IF = 700 ma | | 4.5 | | ° C./W |

The irradiation parameters were set according to the objective of the POC: to verify the ability of the blue light to eradicate a colony of *C. albicans* yeast. The LED current was set to 350 mA—that yielded a device power flux of 25 $mW/cm^2$ over the irradiated wells. For the planned 3-hour irradiation period of the study, this power flux provides an energy flux of 275 $Joules/cm^2$ or a total energy 700 joules per irradiated well.

31
32

Study Protocol

Introduction: Vulvovaginal Candidiasis (VVC) is a fungal infection that causes irritation, discharge and itchiness of the vaginal tissues. It is estimated that fungal infections occur in over a billion women each year. Zero-*Candida* is developing medical treatments for recurrent vulvovaginal candidiasis (VVC), incorporating irradiation of antimicrobial blue light (aBL). aBL, has an intrinsic ability to inactivate pathogens, through excitation of naturally occurring endogenous photosensitizers in pathogens cells. In the present study, we investigate the effectiveness of aBL of the Zero *Candida* device for in vitro inactivation of *Candida Albicans.*

Study Objectives: Establish the effects of blue light irradiation properties of the ILTD on the eradication of *Candida albicans.*

ABBREVIATIONS

| | |
|---|---|
| aBL | Antimicrobial Blue light |
| C. albicans | Candida Albicans |
| CFU | Colony-Forming Unit. |
| PCB | Printed Circuit Board |
| POC | Proof of Concept |
| VVC | Recurrent Vulvovaginal Candidiasis |
| RT | Room Temperature |
| SRF | Study results form |
| TBD | To Be Defined |
| TSB | Tryptic Soy Broth |

The study is exploratory and is aimed to ascertain the order of magnitude of the effect of continuous irradiation on *C. albicans* culture. Analysis of the test results will provide insights of the tested properties and help in forming a therapy model for further testing.

Materials

*C. albicans* culture-grown in a TSB medium and diluted in sterile saline-yeasts are seeded into wells of a sterile 24-well microplate. 2 mL of *C. albicans* solution, diluted to a concentration of $10^6$ CFU/ml, are filled into each of the 4 wells in the line to be irradiated.

Rationale: saline is used for dilution to stabilize the yeast concentration throughout the test, so that the yeast concentration changes reflect solely the irradiation effect.

Test Configuration

Test Device: 24-well microplate, arranged in 6×4 configuration, each ~16 mm diameter, 12 mm deep. Two lines of 4 wells are irradiated by Zero *Candida*'s lighting device and other wells serve as non-irradiated control. A line of 4 wells between the irradiated lines is intentionally left empty, to avoid cross effects. Since some evaporation is expected during the test, the volume in each well will be measured and documented pre- and post-irradiation. These well-volumes will be used to factor the test results. The results will be documented in the SRF (Study Report Form).

The POC Study System

The POC study system is designed around the test device—a 24-well microplate—mounted on the Study Device that consists of a PCB that is connected to 2 LED strips, which are mounted on top of a standard 24-well microplate. The LEDs have a wavelength of 405 nm. Various irradiation patterns are controlled centrally for each line by the Control Box. The power for the first test is set at about 0.7 mW/cm². An aluminum heatsink air-fans are added to the Study Device to control the LEDs temperature rise due to the irradiation power.

The irradiation power will be measured via the supply current for each line of LEDs and documented in the study form (SRF). The Study Device will be placed in a darkened hood, in a water bath, so that the microplate bottom will be 6 mm below the water level. Care shall be taken not to flood the microplate.

The water bath-provided by the lab-shall maintain constant temperature of 36° C.+/−1° C. by water circulation and temperature control in order to keep the temperature of the microplate between 37° C. and 39° C. The water temperature shall be displayed and documented in the SRF.

Procedure Summary for aBL Irradiation

The wells will be irradiated by the Test System for 3 hrs, at 36° C. Post irradiation, the content of each well will be diluted 6 times at 10gIO and spread on separate Petri dishes. The separate dishes will be incubated for 3 days, after which the colonies will be counted to determine the irradiation efficacy factor.

Study and Results

Objective: Test the ability of the POC Study Device (Blue Light, at a wavelength of 405 nm) to cause up to a 6 $\log_{10}$ reduction of *C. albicans* colony (measured by a filtration method according to Hy Laboratories SOP No. 10-003).

Experiment Procedures: *C. albicans* line ATCC 10231 were seeded on a 24 well transparent plate and were irradiated by blue-light emitted by the POC Study Device. Following a 3-hour irradiation period, over 99.999% of the *C. albicans* were eradicated.

To confirm that this >6 $\log_{10}$ eradication was due only to the irradiation by blue light, two additional experiments were conducted:

a) Repetition of the first experiment, but with no irradiation—to verify the viability of the ATCC 10231 colony and procedures; and b) Measurement of the area irradiated by the POC irradiation device—to check the possibility that high power flux of light emitted by the POC irradiation device reached the control wells.

Example 3: Experiment 1 (24 Nov. 2022)

The *C. albicans* cultures were grown on SDA (Sabouraud Dextrose Agar) plates and then diluted with sterile saline solution to 1.29×10⁶ CPU per ml suspension (CPU=Colony Forming Units).

The total eradication of *C. albicans* raised the question whether the blue light was the sole cause for the eradication results.

The temperature measurements of the irradiated wells throughout the irradiation period provided an answer to the Heat concern (see Table 3): The equilibrium temperature in an irradiated well at 30 min. post test-start was 29.8° C. and reached 31.8° C. at the test-end—just 2° C. difference. The highest temperature recorded was 33° C. (120 min. after start)—only 3.2° C. over the first equilibrium measurement.

TABLE 3

Microplate wells and bath temperatures during the study

| Time (min) | Well Temp. (° C.) | Bath Temp (° C.) |
|---|---|---|
| 0 | 24.7 | 36.2 |
| 30 | 29.8 | 36.0 |
| 60 | 30.0 | 36.0 |
| 90 | 31.4 | 36.0 |

TABLE 3-continued

| Microplate wells and bath temperatures during the study | | |
|---|---|---|
| Time (min) | Well Temp. (° C.) | Bath Temp (° C.) |
| 120 | 33.0 | 34.5 |
| 150 | 31.0 | 34.0 |
| 180 | 31.8 | 34.1 |

The evaporation levels in the irradiated wells were 31% on average—a level that is biologically insignificant in terms of culture viability. The average evaporation of the non-irradiated (control) wells was 13.75%—indicating that the bath temperature and the LED's are probably the main causes of evaporation.

Example 4: Experiment 2 (29 Nov. 2022)

Objective: The objective of this experiment was to verify the viability of the *C. albicans* culture that was used in Experiment I and the procedures for handling it. Hence, Experiment 2 was conducted identically to Experiment 1, except that no wells were exposed to blue light.

Method: The POC procedure of Experiment I was repeated on the 29 Nov. 2022, with a new culture of *C. albicans*, except that no irradiation device was operated. The culture was grown on SDA plates and diluted with sterile saline solution resulting in a suspension of $7.07 \times 10^5$ CFU/ ml. The 24-well plate was populated with PC and NC located as on Experiment 1: For Positive Control: 4 replicates of PC, each containing 2 ml of $1.41 \times 10^6$ CFU of *C. albicans*; For Negative Control: 2 replicates of NC, each containing 2 ml of sterile saline solution.

The plate was placed in a water bath adjusted to 36° C. for 3 hours—the same conditions as on Experiment 1 except the irradiation. The water bath cover was covered with aluminum foil to create darkness through the 3-hour incubation; The volume in each well was measured before and after the 3 hours. No significant evaporation was observed.

The suspensions were then filtered through 0.45 µm membrane and the membrane was placed on SDA+Chloram plate. The samples were diluted serially and each SDA and SDA+Chloram plates were incubated at 20-25° C. for 3 days.

Following the 3-day incubation, the concentration of *C. albicans* was measured for each plate. The plates originating from the PC wells yielded *C. albicans* concentrations between $2.96$-$3.88 \times 10^5$ CFU/ml. The NC wells yielded no *C. albicans* growth. That concentration was about $0.6 \log_{10}$ lower than the original concentration of $1.41 \times 10^6$ CFU/2 ml of *C. albicans* in each well. This reduction was attributed mainly to the inherently wide deviation range of the method (HyLabs SOP No. 10-003-13 allows for a standard deviation of 25%).

Conclusion: The post incubation *C. albicans* concentrations are considered normal and indicate that the ATCC line and handling procedures were viable and did not contribute to the total eradication of *C. albicans* in Experiment 1.

Example 5: Microbiological Analysis

Method: Testing the ability of the ILTD (Blue-light, at a wavelength of 405 nm) to cause $6 \log_{10}$ reduction of *C. albicans* ATCC 10231 based on the filtration method according to HyLabs SOP No. 10-003.

Procedure: on the 24 Nov. 2022, *C. albicans* ATCC 10231 culture and a 24 well transparent plate were used. The *C.*

*albicans* culture were monitored on SDA plates with sterile saline solution resulting in $1.29 \times 10^6$ CFU per ml suspension.

The wells of the plate were filled as follows: for test-2 ml containing $2.58 \times 10^6$ CFU of *C. albicans* exposed to blue-light. There were 5 replicates; 4 replicates with *C. albicans* for positive control containing 2 ml with the same concentration as the test, but without the blue-light exposure; and 2 replicates without *C. albicans* for negative control containing 2 ml saline. 3 additional wells contained 2 ml reverse osmosis water to check the temperature.

The plates were exposed to the Zero *Candida* device and the entire apparatus (plate and device) was placed in a water bath adjusted to 36° C. for 3 hours. The water bath cover was disinfected with 70% alcohol wipes before the incubation step and covered with aluminum foil to create darkness through the 3 hours incubation step.

In order to check the degree of evaporation, after 3 hours incubation, the volume in each well was measured. Each well was filtered through a 0.45 µm membrane and the membrane was placed on SDA+Chloram plate. For the positive control wells, assuming that no reduction in the *C. albicans* concentration should be observed, serial dilutions were conducted and each dilution was filtered separately in order to reach a readable count. For the test wells, since a reduction in the *C. albicans* concentration was expected but at an unknown degree, serial dilutions were conducted and each dilution (including the rest of the un-diluted sample) was filtered separately in order to reach a readable count. All SDA and SDA+Chloram plates were incubated as 20-25° C. up to 5 days, which are the optimal conditions of growth for the yeast on the specific media plate.

Although *C. albicans* were viable before the incubation in the water bath and the exposure to the Zero *Candida* device (ILTD), the results showed that no growth of *C. albicans* in the test samples (see results), raising the possibility that the 3 hours incubation step at 36° affected the viability of *C. albicans* to the extent of $6 \log_{10}$ reduction.

To rule out, or to confirm this possibility, the procedure was repeated on the 29 Nov. 2022 without exposure to the ILTD using a new culture of *C. albicans*. The culture was monitored on SDA plates and diluted with sterile saline solution resulting in $7.07 \times 10^5$ CFU per ml suspension.

The plate was placed in a water bath adjusted to 36° C. for 3 hours without the ILTD. The water bath cover was disinfected with 70% alcohol wipes before the incubation step and covered with aluminum foil to create darkness through the 3 hours incubation step.

After 3 hours of incubation, the volume in each well was measured, and the content was filtered through a 0.45 µm membrane and the membrane was placed on SDA+Chloram plate. For the positive control wells, assuming that no reduction in the *C. albicans* concentration should be observed, serial dilutions were conducted and each dilution was filtered separately in order to reach a readable count. All SDA and SDA+Chloram plates were incubated as 20-25° C. up to 5 days.

Results

The starting volume in each well was 2 ml/At the end of the experiment (After 3 hours), the volume of each well was measured again. The calculated average volume of the five test wells that were exposed to the blue-light was 1.38 ml, resulting in an average evaporation of 31%, probably due to the mild heating from the LEDs. The average volume of the rest of the wells (positive- and negative-controls) at the end of the experiment was 1.73 ml, resulting in an average evaporation of 13.75%.

TABLE 4

| Results of 24.11.2022 experiment using the ILTD | | | |
|---|---|---|---|
| Replica | Test (CFU/well) | Pos. control (CFU/well) | Neg. control (CFU/well) |
| 1 | 0 | 0 | 0 |
| 2 | 0 | 0 | 0 |
| 3 | 0 | 0 | NA |
| 4 | 0 | 0 | NA |
| 5 | 0 | NA | NA |
| Average CFU/sample | 0 | 0 | 0 |

According to the above, no growth of *C. albicans* was seen in the test and positive samples.

TABLE 5

| Results of 29.11.2022 experiment without the ILTD | | |
|---|---|---|
| Replica | Pos. control (CFU/well) | Neg. control (CFU/well) |
| 1 | $3.88 \times 10^5$ | 0 |
| 2 | $3.94 \times 10^5$ | 0 |
| 3 | $3.96 \times 10^5$ | NA |
| 4 | $3.36 \times 10^5$ | NA |
| Average CFU/sample | $3.54 \times 10^5$ | 0 |

According to the above, it seems that the 3-hours incubation of *C. albicans* did not cause a 6 $\log_{10}$ reduction. Since the starting concentration was $1.41 \times 10^6$ CFU per 2 ml of *C. albicans* in each well. A slight decrease in the concentration of *C. albicans* was seen (average of 0.6 $\log_{10}$), which can be explained either by the lack of growth medium in the 3-hours incubation, and/or by the uncertainty of the method (standard deviation of 25% according to HyLab SOP No. 10-003-13).

Conclusions: there was no growth of *C. albicans* in the positive control and the test wells following exposure to the ILTD. At the same conditions, without the presence of the ILTD, the viability of the *C. albicans* was not affected to the extent of 6 $\log_{10}$.

According to the results above, a 3-hours exposure to the ILTD yielded a 6.4 $\log_{10}$ reduction from the initial inoculum.

Structural details of the invention are shown to provide a fundamental understanding of the invention, the description, taken with the drawings, making apparent to those skilled in the art how the several forms of the invention may be embodied in practice.

It is to be understood that the embodiments described hereinabove are cited by way of example, and that the present invention is not limited to what has been particularly shown and described hereinabove. Device elements/components described may be altered according to need and additional known elements of similar systems, which are not explicitly mentioned or exemplified herein, may be added.

Where methods described above indicate certain events occurring in certain order, the ordering of certain events may be modified. Additionally, certain of the events may be performed concurrently in a parallel process when possible, as well as performed sequentially as described above. In addition, method steps associated with the system and process can be rearranged and/or one or more such steps can be omitted to achieve the same, or similar, results to those described herein.

Communications between systems, devices and components described above are assumed to be performed by software modules and hardware devices known in the art. Processing elements and memory storage, such as databases, may be implemented so as to include security features, such as authentication processes known in the art.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the invention includes other combinations of fewer, more or different elements, which are disclosed above even when not initially claimed or mentioned in such combinations. A teaching that two elements are combined is further to be understood as also allowing for a combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

The invention claimed is:

1. An intravaginal light-based treatment device (ILTD) (100) for treating patient's vaginal disorders, the device comprising:
   a) a main body (101) having a cylindrical shape and a longitudinal axis;
   b) a light source (102);
   c) a power source (103);
   d) a coating (104) over said main body (101); and
   e) a flexible tether (105),
   wherein
      said light source emits pulsed light having at least one predefined wavelength suitable for treating said vaginal disorders, and said main body (101) and coating (104) configured to allow said light to pass through and reach vaginal tissue;
      said light source emits said light at predefined intervals and intensities suitable for treating said vaginal disorders;
      said flexible tether (105) is a heat-conduit that removes excess heat generated by said ILTD outside from the vagina;
      said flexible tether (105) is a flexible wire connected to said main body (101) and is configured to retract the ILTD outside from the patient's vagina;
      said coating (104) includes rough regions that are anti-slip regions (106) designed to assist the ILTD to remain in place, as well as in the right/desired position and orientation within the vagina, thereby directing the emitted light in the desired direction; and
      said anti-slip regions (106) comprise protrusions (116) extending along the longitudinal axis of the main body, and configured to maintain the ILTD in place after insertion, in the desired position and orientation, thereby facilitating the emitted light to be emitted in the desired direction.

2. The ILTD of claim 1, further comprising one or more active agents selected from: moisture materials, hormones, therapeutics, buffer material, and/or biome, or any combination thereof, wherein:
   said device releases said one or more active agents into the vagina; and
   said light source emits said light either constantly or at predefined intervals and intensities suitable for treating said vaginal disorders.

3. The ILTD of claim 1, wherein said coating (104) is removable.

4. The ILTD of claim 1, further comprising a thermometer or temperature-sensor designed to measure the temperature inside the vagina, a camera designed to capture images of the vagina's inner walls, pH-sensor or pH-meter (109) designed to measure the pH inside the vagina, a moisture sensor, and a data-transmitter designed to transmit data from said camera, pH-meter (109) and thermometer to a remote computing system,
   wherein the ILTD optionally comprises or is associated-with a computing system comprising a processor and a memory communicatively coupled to the processor, the memory comprising computer-readable instructions that when executed by the processor cause the computing system to implement a method of treating patient's vaginal disorders, the method comprising any combination of the following:
      activating and deactivating said light source (102);
      taking images or movies;
      detecting bleeding;
      measuring pH, temperature and/or moisture in the vagina; and
      releasing active agents into the vagina.

5. The ILTD according to claim 4, for diagnosing various disorders or conditions of a patient's vagina.

6. A kit for monitoring and diagnosing a patient's vaginal health condition, the kit comprises one or more intravaginal light-based treatment device (ILTD) (100) as defined in claim 4, wherein the kit further comprises: (i) two or more coatings (104) designed to be used by said ILTD, said coatings (104) are the same or different; and/or (ii) a conduit designed to assist in insertion of the ILTD into a patient's vagina.

7. A method of diagnosing or monitoring a vaginal disorder in a woman, the method comprising:
   a) providing an intravaginal light-based treatment device (ILTD) (100) as defined in claim 4;
   b) inserting said ILTD into the vagina of said woman;
   c) activating said ILTD thereby gathering data from within the vagina and transmitting the data to a remote computing system; and
   d) analyzing said data and diagnosing said vaginal disorder or monitoring its condition.

8. The method according to claim 7, further comprising treating said vaginal disorder based on the diagnosis or condition thereof.

9. The ILTD of claim 1, wherein said coating (104) comprises or is coated-with: (i) buffer material designed to be released into the vagina to adjust pH inside the vagina; (ii) one or more therapeutics, designed to be released into the vagina according to need; or (iii) dimethyl sulfoxide (DMSO),
   wherein said therapeutics are designed to be released automatically (i) by diffusing therethrough; (ii) due to dissolving of the coating's material; (iii) according to environment pH and/or temperature; or (iv) according to instructions received from a computing system according to a predefined treatment regimen.

10. The ILTD of claim 1, wherein said main body (101) comprises: (i) buffer material designed to be released into the vagina to adjust pH inside the vagina; (ii) one or more therapeutics designed to be released into the vagina according to need; or (iii) dimethyl sulfoxide (DMSO),
   wherein said therapeutics are designed to be released automatically (i) by diffusing therethrough; (ii) due to dissolving of the coating's material; (iii) according to environment pH and/or temperature; or (iv) according to instructions received from a computing system according to a predefined treatment regimen.

11. The ILTD of claim 1, wherein said light source (102) is designed to emit: (i) light at variable wavelengths and intensities according to a predefined treatment regimen; (ii) red-, green-, or blue-visible light, or any combination thereof; (iii) infrared (IR) and ultraviolet (UV) light, or both; or (iv) laser light, or any combination thereof.

12. The ILTD of claim 1, wherein said main body (101) holds: (i) said light source (102); or (ii) said power source (103), or both.

13. The ILTD of claim 1, wherein said light source (102) comprises multiple light points spread along the main body (101) and designed to emit light in all directions.

14. The ILTD of claim 1, wherein said ILTD is disposable, and said light source (102) is a chemical, non-electric, light source, and activation of the light source (102) is done by mixing two or more reagents together immediately prior to use of the ILTD.

15. The ILTD of claim 1, wherein said ILTD is: (i) disposable, and said main body (101) and said coating (104) constitute a single unit holding said light source (102) and said power source (103).

16. The ILTD of claim 1, wherein said light source (102) is inside said main body (101) and said power source (103) is in an external casing (107), and said tether (105) is used to transfer power from said power source (103) to said light source (102).

17. The ILTD of claim 1, wherein said main body (101) is hollow and said light source (102) and said power source (103) are both in an external casing (107), and said tether (105) is used to transfer light from said external casing (107) to said main body (101).

18. The ILTD of claim 1, for use in treating patient's vaginal disorders.

19. A kit for treating patient's vaginal disorders, the kit comprises one or more intravaginal light-based treatment device (ILTD) (100) as defined in claim 1, wherein the kit further comprises: (i) two or more coatings (104) designed to be used by said ILTD, said coatings (104) are the same or different; and/or (ii) a conduit designed to assist in insertion of the ILTD into a patient's vagina.

20. A light-based method of treatment or prophylaxis of a vaginal disorder in a woman, the method comprising:

a) providing an intravaginal light-based treatment device (ILTD) (100) as defined in claim 1;

b) inserting said ILTD (100) into the vagina of said woman; and c) activating said ILTD thereby illuminating the vagina's interior, wherein said ILTD optionally comprises one or more active agents selected from: moisture materials, hormones, therapeutics, buffer material, and/or biome, or any combination thereof, said method further comprising releasing an effective amount of said one or more active agents into the vagina.

21. The light-based method according to claim 20, wherein activating said ILTD is carried out by: (i) pressing or turning an activation switch; (ii) removing a protective cover from the ILTD or said coating (104); (iii) removing an electric barrier from the power source (103) thereby enabling passage of power therefrom to the light source (102); or (iv) breaking or removing a barrier within the ILTD thereby mixing two or more reagents together, which results with generation of light.

22. The light-based method according to claim 20, further comprising a step of replacing one ILTD with another daily, wherein all the ILTDs have the same or different activity compared to the previously used ILTD.

23. The ILTD of claim 1, wherein the anti-slip regions (106) include grooves.

* * * * *